(12) United States Patent
Lollo et al.

(10) Patent No.: US 11,285,192 B2
(45) Date of Patent: Mar. 29, 2022

(54) FORMULATION INCLUDING A COMBINATION OF BETA-ENDORPHIN AND ADRENOCORTICOTROPIC HORMONE

(71) Applicant: Adamis Pharmaceuticals Corporation, San Diego, CA (US)

(72) Inventors: Charles Peter Lollo, San Diego, CA (US); Dennis J. Carlo, San Diego, CA (US)

(73) Assignee: Adamis Pharmaceuticals Corporation, San Diego, CA (US)

( * ) Notice: Subject to any disclaimer, the term of this patent is extended or adjusted under 35 U.S.C. 154(b) by 0 days.

(21) Appl. No.: 17/008,202

(22) Filed: Aug. 31, 2020

(65) Prior Publication Data

US 2021/0100878 A1 Apr. 8, 2021

Related U.S. Application Data

(63) Continuation-in-part of application No. PCT/US2020/022473, filed on Mar. 12, 2020.

(60) Provisional application No. 62/981,379, filed on Feb. 25, 2020, provisional application No. 62/818,034, filed on Mar. 13, 2019.

(51) Int. Cl.
*A61K 38/35* (2006.01)
*A61K 38/33* (2006.01)

(52) U.S. Cl.
CPC ............. *A61K 38/35* (2013.01); *A61K 38/33* (2013.01); *A61K 2300/00* (2013.01)

(58) Field of Classification Search
CPC ..... A61K 2300/00; A61K 38/33; A61K 38/35
See application file for complete search history.

(56) References Cited

U.S. PATENT DOCUMENTS

| | | |
|---|---|---|
| 2009/0004246 A1 | 1/2009 | Woolfson et al. |
| 2012/0114706 A1 | 5/2012 | Sarkar |
| 2013/0115640 A1 | 5/2013 | Tumlin et al. |
| 2014/0072530 A1* | 3/2014 | McIntosh ............... A61P 43/00 424/85.2 |

FOREIGN PATENT DOCUMENTS

| | | |
|---|---|---|
| WO | 1988/005297 A1 | 7/1988 |
| WO | 2020/186108 A1 | 9/2020 |

OTHER PUBLICATIONS

Wendy Gilmore, B-Endorphin protects mice from neurological disease induced by the murine coronavirus MHV-JHM Journal of Neuroimmunology, 48 (1993) 81-90.*
Barry G Arnason, Mechanisms of action of adrenocorticotropic hormone and other melanocortins relevant to the clinical management of patients with multiple sclerosis, Multiple Sclerosis Journal, 2012.*
Kathleen M. Foley, B-Endorphin: Analgesic and hormonal effects in humans, Proc. Natl. Acad. Sci. USA vol. 76, No. 10, pp. 5377-5381, Oct. 1979.*
I Izquierdo, R D Dias , Effect of ACTH, epinephrine, beta-endorphin, naloxone, and of the combination of naloxone or beta-endorphin with ACTH or epinephrine on memory consolidation, 1983, pyschoneuroendocrinology.*
Citterio A, La Mantia, Corticosteroids or ACTH for acute exacerbations in multiple sclerosis (Review), Cochrane Database of Systematic Reviews 2000, Issue 4.*
Christen Kutz, H.P. Acthar Gel (repository corticotropin injection) treatment of patients with multiple sclerosis and diabetes, Ther Adv Chronic Dis 2016, vol. 7(4) 190-197.*
Adrenocorticotropic Hormone (ACTH): MedlinePlus Medical Test. National Institutes of Health/U.S. National Library of Medicine, page last updated on Mar. 24, 2020. https://medlineplus.gov/labtests/adrenocorticotropic-hormone-acth/. Website accessed on Jul. 7, 2020, 4 pp.
Aluri et al., Three dimensional modelling of beta endorphin and its interaction with three opioid receptors. Journal of Computational Biology and Bioinformatics Research, 4(4): 51-57 (2012).
Berkovich et al., Mechanisms of action of ACTH management of relapsing forms of multiple sclerosis. Therapeutic Advances in Neurological Disorders, 7(2): 83-96 (2014).
Beta Endorphin—an overview. ScienceDirect, accessed Jul. 2, 2020. https://www.sciencedirect.com/topics/pharmacology-toxicology-and-pharmaceutical-science/beta-endorphin.
Cortez et al., Infantile spasms and down syndrome: a new animal model. Pediatric Research, 65(5): 499-503 (2009).
Cusick et al., Acthar gel treatment suppresses actute exacerbations in a murine model of relapsing-remitting multiple sclerosis. Autoimmunity, 48(4):222-230 (2015).
Gettig et al., H.P. Acthar gel and Cosyntropin Review: Clinical and Financial Implications P&T, vol. 34, No. 5, pp. 250-257 (2009).
Gironi et al., β endorphin concentrations in PBMC of patients with different clinical phenotypes of multiple sclerosis. J Neurol Neurosurg Psychiatry, 74:495-497 (2003).
H.P. Acthar Gel Dosage Guide. https//www.drugs.com/dosage/h-p-acthar-gel.html. Website accessed Jul. 10, 2020.
International Patent Application No. PCT/US2020/048813 filed on Aug. 31, 2020.
International Search Report and Written Opinion, dated Jun. 19, 2020, for International Application No. PCT/US2020/022473 filed on Mar. 12, 2020.
International Search Report and Written Opinion, dated Nov. 27, 2020, for International Application No. PCT/US2020/048813 filed on Aug. 31, 2020.

(Continued)

*Primary Examiner* — James H Alstrum-Acevedo
*Assistant Examiner* — Erinne R Dabkowski
(74) *Attorney, Agent, or Firm* — K&L Gates LLP; Louis C. Cullman; Hal Gibson

(57) ABSTRACT

The present specification provides compositions of β-endorphin and adrenocorticotropic hormone (ACTH). These compositions are useful in methods of treating disease.

8 Claims, 7 Drawing Sheets
Specification includes a Sequence Listing.

(56) References Cited

OTHER PUBLICATIONS

Nagamitsu et al., Decreased cerebrospinal fluid levels of beta-endorphin and ACTH in children with infantile spasms. J Neural Transm (Vienna), 108(3):363-371 (2001).
Pollack, Andrew. Questcor finds profits, at $28,000 a vial. The New York Times, Dec. 29, 2012 (11 pp).
Prescribing Information for CORTROSYN® for injection, revised Sep. 2010.
Prescribing Information for H.P. Acthar® Gel, revised Apr. 2018.
Repository Corticotropin Injection (H.P. Acthar Gel), Policy No. MP-2.162. Capital Blue, Medical Policy, Issue Date May 10, 2011 (11 pp).
Shrihari, TG. Beta-Endorphins: A novel anti-inflammatory activity. EC Pharmacoloy and Toxicology, 7.6:481-484 (2019).
Synacthen (Zinc Hydroxide). RxMed.com, Copyright © 1997-2019 RxMed: Diseases and Preparations' Description.
Warren et al., Multiple sclerosis and diabetes mellitus: Further evidence of a relationship. Canadian Journal of Neurological Sciences, vol. 9, pp. 415-419 (1982).
Wikipedia, Adrenocorticotropic hormone (medication). https://enwikipedia.org/wiki/Adrenocorticotropic_hormone_(medication), last edited on Jan. 28, 2019, accessed on Feb. 1, 2019, 8 pp.
Brooks, Megan. ACTH pulse therapy may benefit breakthrough MS. American Academy of Neurology (AAN) 65th Annual Meeting. Abstract P04.269. Mar. 16-23, 2013. Medscape Medical News 2013, WebMD, LLC.

* cited by examiner

SEQUENCE LISTING

```
<160> NUMBER OF SEQ ID NOS: 11

<210> SEQ ID NO 1
<211> LENGTH: 31
<212> TYPE: PRT
<213> ORGANISM: Homo sapiens

<400> SEQUENCE: 1

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 2
<211> LENGTH: 39
<212> TYPE: PRT
<213> ORGANISM: Homo sapiens

<400> SEQUENCE: 2

Ser Tyr Ser Met Glu His Phe Arg Trp Gly Lys Pro Val Gly Lys Lys
1               5                   10                  15
```

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 3
<211> LENGTH: 31
<212> TYPE: PRT
<213> ORGANISM: Bos taurus

<400> SEQUENCE: 3

Tyr Gly Gly Phe Met Thr Ser Glu Lys Ser Gln Thr Pro Leu Val Thr
1               5                   10                  15

Leu Phe Lys Asn Ala Ile Ile Lys Asn Ala His Lys Lys Gly Gln
            20                  25                  30

<210> SEQ ID NO 4
<211> LENGTH: 39
<212> TYPE: PRT
<213> ORGANISM: Bos taurus

<400> SEQUENCE: 4

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Gln Ala Phe Pro Leu Glu Phe
        35

<210> SEQ ID NO 5
<211> LENGTH: 31
<212> TYPE: PRT
<213> ORGANISM: Sus scrofa

<400> SEQUENCE: 5

Tyr Gly Gly Phe Met Thr Ser Glu Lys Ser Gln Thr Pro Leu Val Thr
1               5                   10                  15

Leu Phe Lys Asn Ala Ile Val Lys Asn Ala His Lys Lys Gly Gln
            20                  25                  30

<210> SEQ ID NO 6
<211> LENGTH: 39
<212> TYPE: PRT
<213> ORGANISM: Sus scrofa

<400> SEQUENCE: 6

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Leu Ala
            20                  25                  30

Glu Ala Phe Pro Leu Glu Phe
        35

<210> SEQ ID NO 7
<211> LENGTH: 39
<212> TYPE: PRT
<213> ORGANISM: Sus scrofa

<400> SEQUENCE: 7

Ser Tyr Ser Met Glu His Phe Arg Trp Gly Lys Pro Val Gly Lys Lys
1               5                   10                  15

Arg Arg Pro Val Lys Val Tyr Pro Asp Gly Ala Glu Asp Gln Leu Ala
            20                  25                  30

Glu Ala Phe Pro Leu Glu Phe
            35

<210> SEQ ID NO 8
<211> LENGTH: 31
<212> TYPE: PRT
<213> ORGANISM: Mus musculus

<400> SEQUENCE: 8

Tyr Gly Gly Phe Met Thr Ser Glu Lys Ser Gln Thr Pro Leu Val Thr
1               5                   10                  15

Leu Phe Lys Asn Ala Ile Ile Lys Asn Ala His Lys Lys Gly Gln
            20                  25                  30

<210> SEQ ID NO 9
<211> LENGTH: 39
<212> TYPE: PRT
<213> ORGANISM: Mus musculus

<400> SEQUENCE: 9

Ser Tyr Ser Met Glu His Phe Arg Trp Gly Lys Pro Val Gly Lys Lys
1               5                   10                  15

Arg Arg Pro Val Lys Val Tyr Pro Asn Val Ala Glu Asn Glu Ser Ala
            20                  25                  30

Glu Ala Phe Pro Leu Glu Phe
            35

<210> SEQ ID NO 10
<211> LENGTH: 266
<212> TYPE: PRT
<213> ORGANISM: Homo sapiens

<400> SEQUENCE: 10

Met Pro Arg Ser Cys Cys Ser Arg Ser Gly Ala Leu Leu Leu Ala Leu
1               5                   10                  15

Leu Leu Gln Ala Ser Met Glu Val Arg Gly Trp Cys Leu Ser Ser Gln
            20                  25                  30

Cys Gln Asp Leu Thr Thr Glu Ser Asn Leu Leu Glu Cys Ile Arg Ala
            35                  40                  45

Cys Lys Pro Asp Leu Ser Ala Glu Thr Pro Met Phe Pro Gly Asn Gly
        50                  55                  60

Asp Glu Gln Pro Leu Thr Glu Asn Pro Arg Lys Tyr Val Met Gly His
65                  70                  75                  80

Phe Arg Trp Asp Arg Phe Gly Arg Arg Asn Ser Ser Ser Ser Gly Ser
                85                  90                  95

Ser Gly Ala Gly Gln Lys Arg Glu Asp Val Ser Ala Gly Glu Asp Cys
            100                 105                 110

Gly Pro Leu Pro Glu Gly Gly Pro Glu Pro Arg Ser Asp Gly Ala Lys
            115                 120                 125

Pro Gly Pro Arg Glu Gly Lys Arg Ser Tyr Ser Met Glu His Phe Arg
        130                 135                 140

Trp Gly Lys Pro Val Gly Lys Lys Arg Arg Pro Val Lys Val Tyr Pro
145                 150                 155                 160

Asn Gly Ala Glu Asp Glu Ser Ala Glu Ala Phe Pro Leu Glu Phe Lys
                165                 170                 175

```
Arg Glu Leu Thr Gly Gln Arg Leu Arg Glu Gly Asp Gly Pro Asp Gly
            180                 185                 190

Pro Ala Asp Asp Gly Ala Gly Ala Gln Ala Asp Leu Glu His Ser Leu
        195                 200                 205

Leu Val Ala Ala Glu Lys Lys Asp Glu Gly Pro Tyr Arg Met Glu His
        210                 215                 220

Phe Arg Trp Gly Ser Pro Pro Lys Asp Lys Arg Tyr Gly Gly Phe Met
225                 230                 235                 240

Thr Ser Glu Lys Ser Gln Thr Pro Leu Val Thr Leu Phe Lys Asn Ala
                245                 250                 255

Ile Ile Lys Asn Ala Tyr Lys Lys Gly Glu
                260                 265

<210> SEQ ID NO 11
<211> LENGTH: 130
<212> TYPE: PRT
<213> ORGANISM: Homo sapiens

<400> SEQUENCE: 11

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe Lys Arg Glu Leu Thr Gly Gln Arg Leu
        35                  40                  45

Arg Glu Gly Asp Gly Pro Asp Gly Pro Ala Asp Asp Gly Ala Gly Ala
        50                  55                  60

Gln Ala Asp Leu Glu His Ser Leu Leu Val Ala Ala Glu Lys Lys Asp
65                  70                  75                  80

Glu Gly Pro Tyr Arg Met Glu His Phe Arg Trp Gly Ser Pro Pro Lys
                85                  90                  95

Asp Lys Arg Tyr Gly Gly Phe Met Thr Ser Glu Lys Ser Gln Thr Pro
            100                 105                 110

Leu Val Thr Leu Phe Lys Asn Ala Ile Ile Lys Asn Ala Tyr Lys Lys
        115                 120                 125

Gly Glu
    130
```

FORMULATION INCLUDING A COMBINATION OF BETA-ENDORPHIN AND ADRENOCORTICOTROPIC HORMONE

CROSS REFERENCE TO RELATED APPLICATIONS

This application is a continuation-in-part of PCT/US2020/022473, filed Mar. 12, 2020, which claims the benefit of U.S. Provisional Patent Application Nos. 62/818,034, filed Mar. 13, 2019 and 62/981,379, filed Feb. 25, 2020, each of which is incorporated herein by reference in their entirety.

FIELD

The present disclosure is directed to co-formulations of β-endorphin and adrenocorticotropic hormone (ACTH) as well as their use in methods of treating mammalian disease.

BACKGROUND

Extracts from animal pituitary glands have been used since the 1950s to treat numerous disease indications including multiple sclerosis, systemic lupus erythematosus, proteinuria in nephrotic syndrome, polymyositis, symptomatic sarcoidosis, psoriatic arthritis, rheumatoid arthritis, ankylosing spondylitis, severe acute and chronic allergic and inflammatory processes involving the eye, and infantile spasms. These extract products contain hundreds of peptides that mostly derive from pro-opiomelanocortin (POMC). POMC is cleaved in vivo into several major peptides including adrenocorticotropic hormone (ACTH), melanocyte stimulating hormones (α, β, and γ), Lipotropin (β and γ), β-endorphin and Met-Enkephalin. In addition, peptide extracts contain hundreds of peptide forms that are generated by post-translational modifications.

The activity of such preparations has generally been attributed to ACTH and its ability to stimulate the adrenal cortex to secrete cortisol, corticosterone, and aldosterone. In more recent years synthetic analogues of ACTH have been marketed, such as tetracosactide or cosyntropin (e.g., Cortrosyn® by Amphastar; Synacthen® by Mallinckrodt), consisting of the first 24 amino acids of ACTH's 39 amino acids. While this truncated form of ACTH is reported to have the same corticosteroidogenic activity as natural ACTH, this compound has only been approved for diagnostic uses, for screening patients presumed to have adrenal insufficiency; therapeutic efficacy has not been recognized by the Food and Drug Administration. Cosyntropin has been tested as a treatment for infantile spasms but gave poorer outcomes than prednisolone. Moreover, manufacturers of the traditional biologics (which are defined more by the process by which they are made than what the contents of the product are) have suggested that therapeutic efficacy arises in part from additional unidentified components of the pituitary extracts. Indeed, pituitary extracts have effects that go beyond steroidogenesis. Thus, there has existed an unaddressed need for a defined composition reproducing the therapeutic efficacy of the traditional biologic preparation.

SUMMARY

Disclosed herein are compositions, particularly pharmaceutical compositions, comprising β-endorphin and adrenocorticotropic hormone (ACTH) or analogues of one, the other, or both, thereof. In some embodiments the β-endorphin or ACTH have the human sequence of SEQ ID NO: 1 and SEQ ID NO: 2, respectively. In alternative embodiments the β-endorphin or ACTH, have the bovine sequence of SEQ ID NO: 3 and SEQ ID NO: 4, respectively, or the porcine sequence of SEQ ID NO: 5 and SEQ ID NO: 6 or 7, respectively. ACTH and β-endorphin are highly conserved and the native sequences from other species may be considered analogues of one or another of the sequences enumerated herein. In other embodiments, the analogue is a truncation of a natural sequence, for example, ACTH (1-24). Still other analogues incorporate one or more D-amino acids, for example, amino acids 1 to 5 of the N-terminal residues.

In some embodiments, compositions comprising β-endorphin ACTH or analogues thereof do not comprise any active peptides comprising amino acid sequences from other regions of POMC. In some embodiments, compositions comprising β-endorphin and ACTH or analogues thereof do not comprise any other active peptides derived from POMC. In some embodiments, compositions comprising β-endorphin and ACTH or analogues thereof do not comprise α-melanocyte-stimulating hormone (α-MSH), corticotropin-like intermediate lobe peptide (CLIP), β-lipotropin (β-LPH), β-MSH, γ-MSH, or N-POMC, or any combination thereof.

Some compositions are pharmaceutical co-formulations of β-endorphin and ACTH. In some embodiments, the formulation is a repository or depot-forming formulation, for example, an injectable gel. In some embodiments the injectable gel comprises gelatin, for example, 16% gelatin.

In some embodiments, the co-formulation is supplied in a vial. In other embodiments, the co-formulation is supplied in a pre-filled syringe.

Disclosed herein are methods of treating a disease, disorder, or condition comprising administering a co-formulation of β-endorphin and ACTH, use of β-endorphin and ACTH for treating a disease, use of β-endorphin and ACTH in the manufacture of a medicament for treating a disease, and β-endorphin and ACTH for use in treating a disease. Some embodiments further comprise administration of a superoxide dismutase mimetic, for example Tempol (4-oxypiperidol).

In various embodiments, the disease to be treated is an autoimmune disease, an inflammatory disorder, or an allergic disorder. In some embodiments, the disease to be treated is multiple sclerosis, systemic lupus erythematosus, proteinuria in nephrotic syndrome, polymyositis, symptomatic sarcoidosis, psoriatic arthritis, rheumatoid arthritis, ankylosing spondylitis, or severe acute and chronic allergic or inflammatory processes involving the eye. In some embodiments, the disease to be treated is a neurologic or seizure disorder, including various types of childhood epilepsy, for example, infantile spasms (West syndrome), Lennox-Gastaut syndrome, Landau-Kleffner syndrome, and electrical status epilepticus in sleep.

DETAILED DESCRIPTION

Figure 1:
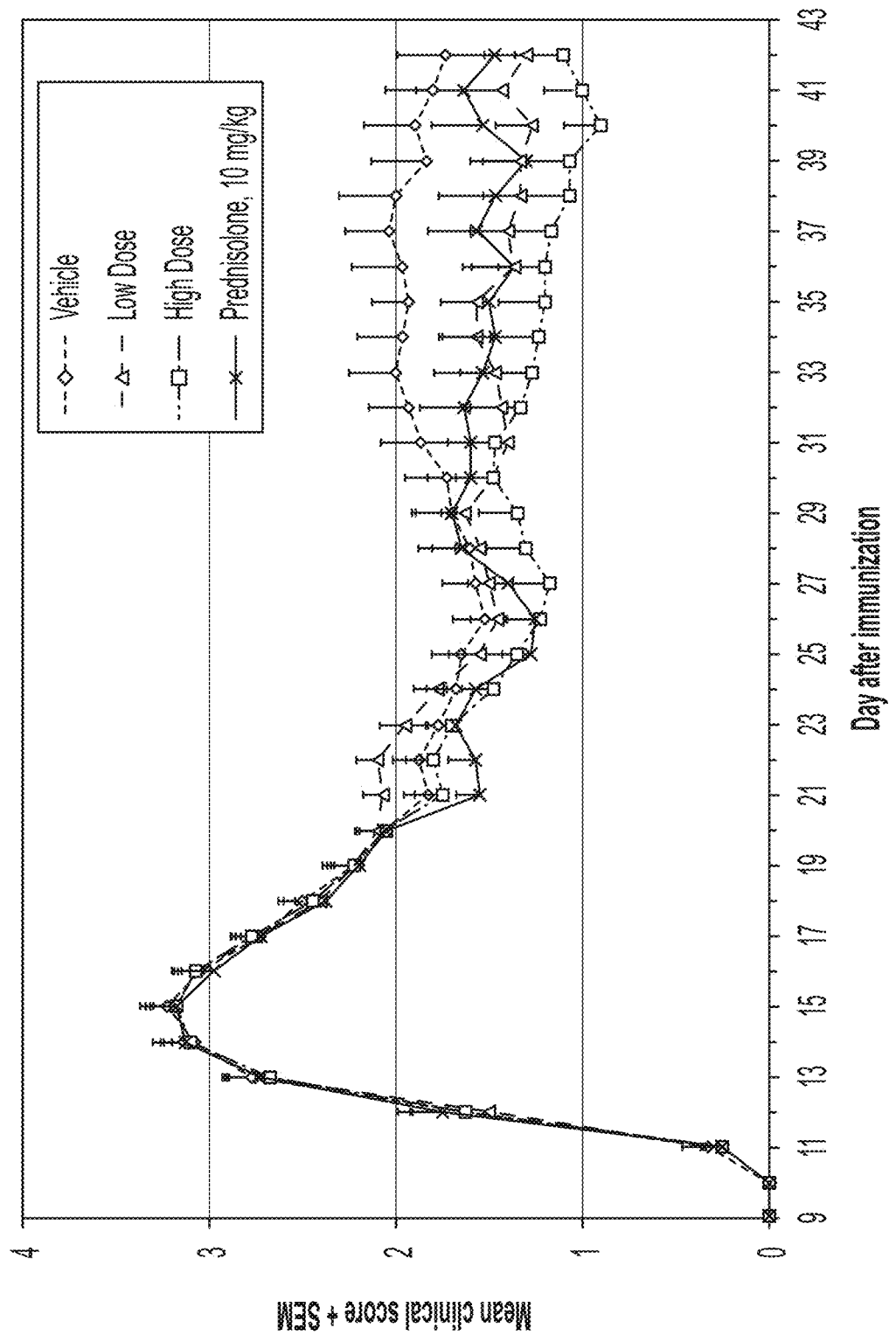
FIG. 1 depicts the change in EAE severity (mean clinical score) over the course of the study for each of the four groups: Vehicle (diamond), ACTH+β-endorphin–Low dose (triangle), ACTH+β-endorphin–High dose (square), and prednisolone (reference treatment; x). In this study low dose was 32 μg ACTH, 16 μg β-endorphin, and high dose was 64 μg ACTH, 32 μg β-endorphin.

Disclosed herein are compositions and formulations comprising β-endorphin and adrenocorticotropic hormone (ACTH) or analogues of either or both thereof. β-endorphin and ACTH are both naturally derived by proteolytic processing from proopiomelanocortin (POMC).

Human POMC is a 241 amino acid polypeptide (SEQ ID NO: 10) which gives rise to multiple recognized peptides. Residues 1-26 are a signal peptide; residues 27-102 are N-terminal peptide of proopiomelanocortin (NPP); residues 77-87 are γ-melanocyte-stimulating hormone (γ-MSH); residues 105-134 are a "potential peptide"; residues 138-176 are ACTH, also called corticotropin; residues 138-150 are α-MSH; residues 156-176 are corticotropin-like intermediate lobe peptide (CLIP); residues 179-267 are β-lipotropin (β-LPH); residues 179-234 are γ-LPH; residues 217-234 are β-MSH; residues 237-267 are β-endorphin; and residues 237-241 are met-enkephalin; as described at UniProtKB-P01189 (COLI_HUMAN).

The sequence of human POMC is:

```
                                          (SEQ ID NO: 10)
         MPRSCCSRSGALLLALLLQASMEVRGWCLSSQ

CQDLTTESNLLECIRACKPDLSAETPMFPGNG

DEQPLTENPRKYVMGHFRWDRFGRRNSSSSGS
```

```
         SGAGQKREDVSAGEDCGPLPEGGPEPRSDGAK

PGPREGKRSYSMEHFRWGKPVGKKRRPVKVYP

NGAEDESAEAFPLEFKRELTGQRLREGDGPDG

PADDGAGAQADLEHSLLVAAEKKDEGPYRMEH

FRWGSPPKDKRYGGFMTSEKSQTPLVTLFKNA

IIKNAYKKGE.
```

In another common numbering system, the N-terminal amino acid residue of ACTH is considered 1, so that ACTH is amino acid residues 1-39, α-MSH is 1-13, CLIP is 19-39, β-LPH is 42-130, γ-LPH is 42-97, β-MSH is 80-97, β-endorphin is 100-130, Met-enkephalin is 100-104, γ-endorphin is 100-116, and α-endorphin is 100-115, of SEQ ID NO:11. Thus the sequence of SEQ ID NO: 11 is:

```
SYSMEHFRWGKPVGKKRRPVKVYPNGAEDESAEAFPLEFKRELTGQRLRE

GDGPDGPADDGAGAQADLEHSLLVAAEKKDEGPYRMEHFRWGSPPKDKRY

GGFMTSEKSQTPLVTLFKNAIIKNAYKKGE.
```

β-endorphin is a 31 amino acid peptide. The sequences of human, bovine, porcine, and murine β-endorphin peptides are each presented in Table 1.

TABLE 1

β-endorphin sequences

| Species | Accession* | Sequence** | SEQ ID NO. |
|---------|-----------|------------|------------|
| Human   | 764134A   | YGGFMTSEKS QTPLVTLFKN AIIKNAYKKG E | 1 |
| Bovine  | NP_776576 | YGGFMTSEKS QTPLVTLFKN AIIKNA<u>H</u>KKG | 3 |
| Porcine | P01192    | YGGFMTSEKS QTPLVTLFKN AI<u>V</u>KNA<u>H</u>KKG | 5 |
| Murine  | NP_032921 | YGGFMTSEKS QTPLVTLFKN AIIKNA<u>H</u>KKG | 8 |

*NCBI Protein Database Accession number
**Differences from the human sequence are bold and underlined The sequences of β-endorphins from many other species have been determined and are readily available from public protein sequence databases and are to be considered analogues of the above disclosed peptides to the extent that they differ. Various embodiments of the herein disclosed compositions and formulations may specifically include one or more of the above peptides (in combination or as alternatives), or an analogue thereof. Other embodiments of the herein disclosed compositions and formulations specifically exclude one or more of the above peptides, or analogues thereof.

β-endorphin is concentrated in the anterior pituitary and pars intermedia, but also widely distributed throughout the body and has been detected in nervous tissue as well as adrenals, heart, liver, and placenta. Concomitant with its broad distribution, the physiological activity of β-endorphin directly or indirectly includes neurotransmitter functions, suppressive effects on respiration, analgesia, maintenance of cardiovascular homeostasis, and even regulation of T- and B-cell function in the immune system. β-endorphin's activity is mediated through classical μ, δ and κ opioid receptors and perhaps a more selective epsilon receptor. β-endorphin, like Met-enkephalin, contains the amino acid sequence YGG (residues 1-3) and binds to opioid receptors (μ, δ, and κ) which mediate its physiologic functions. However, the signaling pathways associated with β-endorphin's roles in the pathophysiology of pain management, obesity, and even immunological responsiveness have not been fully described. In some embodiments, β-endorphin analogues comprise the YGG subsequence.

Other analyses of β-endorphin reveal that YGG (residues 1-3 of SEQ ID NOs: 1, 3, 5, and 8) and QTPLV (residues 11-15 of SEQ ID NOs: 1, 3, 5, and 8) are important for binding to the human μ opioid receptor; K9, QTPLV (residues 11-15 of SEQ ID NOs: 1, 3, 5, and 8), FK (residues 18-19 of SEQ ID NOs:1, 3, 5, and 8), and K29 are important for binding to the human δ opioid receptor; and YGGF (residues 1-4 of SEQ ID NOS: 1, 3, 5, and 8), T6, K9, F18, I22, A26, Y27, K29 and E31 are important for binding to the human κ opioid receptor. (Individual conserved residues are denoted simply as the amino add and the residue position, so that K9 indicates the lysine that is the ninth residue.) It is noted that Y27 and E31 are not conserved across species; apparently these substitutions can be tolerated, or the activities of the non-human β-endorphins in human systems are not crucially dependent on binding to the human κ opioid receptor. In various embodiments, β-endorphin analogues comprise one, some, or all of these conserved subsequences or individual amino acid residues.

ACTH is a 39 amino acid peptide. The sequences of human, bovine, porcine, and murine ACTH peptides are each presented in Table 2.

kephalin, γ-endorphin, and α-endorphin, but does not refer to degradants of ACTH or β-endorphin. In various embodiments, ACTH and β-endorphin, or analogues thereof, together make greater than 90%, 95%, 98%, 99%, 99.5%, 99.8%, 99.9% or 99.99% w/w of the peptides that can be derived from POMC that are present in a disclosed composition or formulation. In various embodiments, ACTH and β-endorphin, or analogues thereof, together make greater than 90%, 95%, 98%, 99%, 99.5%, 99.8%, 99.9% or 99.99%, on a molar basis, of the peptides that can be derived from POMC that are present in a disclosed composition or formulation.

ACTH acts through the melanocortin receptor 2 (MC2R) which is mainly found in the zona fasiculata of the adrenal cortex. By binding to this receptor, ACTH stimulates production of glucocorticoids by adrenocortical cells. This binding is dependent on the KKRRP sequence (residues 15-19 of SEQ ID NOs: 2, 4, 5, 7, and 9) in ACTH, which is not found in other peptides derived from POMC. MC2R is also found on white and brown adipocytes, consistent with ACTH's observed role in glucose metabolism on osteoblasts, and in the skin. ACTH also contains the sequence HFRW (residues 6-9 of SEQ ID NOs: 2, 4, 5, 7, and 9) which mediates binding to all five of the melanocortin receptors. Collectively, the five melanocortin receptors are involved in a diverse number of physiological functions, including pigmentation, steroidogenesis, energy homeostasis, exocrine secretion, sexual function, analgesia and inflammation. Thus, it is clear that ACTH can have functions beyond steroidogenesis. In some embodiments ACTH analogues comprise the KKRRP (residues 15-19 of SEQ ID NOs: 2, 4,

TABLE 2

ACTH sequences

| Species | Accession* | Sequence** | SEQ ID NO. |
|---------|-----------|------------|------------|
| Human | P01189 | SYSMEHFRWGKPVGKKRRPVKVYPNGAEDESAEAFPLEF | 2 |
| Bovine | AAB59262 | SYSMEHFRWGKPVGKKRRPVKVYPNGAEDESA<u>Q</u>AFPLEF | 4 |
| Porcine | NP_999023 | SYSMEHFRWGKPVGKKRRPVKVYPNGAEDE<u>L</u>AEAFPLEF | 6 |
| Porcine | 560078A† | SYSMEHFRWGKPVGKKRRPVKVYP<u>D</u>GAED<u>QL</u>AEAFPLEF | 7 |
| Murine | AAA37169 | SYSMEHFRWGKPVGKKRRPVKVYPN<u>VAE</u><u>N</u>ESAEAFPLEF | 9 |

*NCBI Protein Database Accession number
**Differences from the human sequence are bold and underlined
†as found in H.P. ACTHAR ® Gel The sequences of ACTH from many other species have been determined and are readily available from public protein sequence databases and are to be considered analogues of the above disclosed peptides to the extent that they differ. Various embodiments of the herein disclosed compositions and formulations may specifically include one or more of the above peptides that can be derived from POMC (in combination or as alternatives), or an analogue thereof. Other embodiments of the herein disclosed compositions and formulations specifically exclude one or more of the above peptides that can be derived from POMC, or analogues thereof. In some embodiments, the disclosed compositions are substantially free of other peptides that can be derived from POMC. As used herein, "peptides that can be derived from POMC" refer to peptides that arise from specific proteolytic processing of POMC, for example, NPP, α-MSH, β-MSH, γ-MSH, CLIP β-LPH, γ-LPH, Met-en- 5, 7, and 9) subsequence, the HFRW (residues 6-9 of SEQ ID NOs: 2, 4, 5, 7, and 9) subsequence, or both.

The ACTH and β-endorphin used to make the herein disclosed compositions and formulations can be obtained by any of several methods. Both of these peptides are small enough that it is commercially feasible to produce them by chemical synthesis using standard techniques. Chemical synthesis offers the advantages of using the human amino acid sequences, avoids exposure to enzymes that might further cleave the desired peptide, and obviates fears about adventitious infectious agents (be they prions, viruses, or bacteria) that can attend biologically sourced material.

Alternatively, they can be purified from pituitary extracts similar to those used in the manufacture of historic and currently marketed ACTH-based products. However, a more extensive purification can be used to obtain each of the peptides in (near) homogenous form. In some embodiments, affinity chromatography can be used. Anti-ACTH and anti-β-endorphin monoclonal antibodies have been successfully made in the past and some are commercially available as laboratory reagents. Thus in some embodiments, the composition or formulation comprising ACTH and β-endorphin is substantially free of other peptides found in pituitary extract. In various embodiments, ACTH and β-endorphin, or analogues thereof, in a disclosed composition or formulation are greater than 90%, 95%, 98%, 99%, 99.5%, 99.8%, 99.9% or 99.99% (w/w) free of other peptides found in pituitary extract. In various embodiments, ACTH and β-endorphin, or analogues thereof, in a disclosed composition or formulation are greater than 90%, 95%, 98%, 99%, 99.5%, 99.8%, 99.9% or 99.99% free of other peptides found in pituitary extract on a molar basis.

ACTH and β-endorphin can also be made using recombinant DNA technology either individually or from a common precursor. Post-translational modification of the final peptide is not necessary, so they may be produced in bacterial or eukaryotic culture systems. The primary translation product can typically have an initiator methionine, which can either be retained or be part of a sequence that can be subsequently cleaved.

However produced, polypeptides are subject to degradation through multiple mechanisms. The presence of small amounts of degradants of ACTH or β-endorphin does not mean that a herein disclosed composition or formulation is not substantially free of other peptides found in pituitary extract or other peptides derived from POMC. In preferred embodiments, the total amount of degradants, or the amount of any single degradant, in a composition or formulation does not exceed a level considered acceptable for a human pharmaceutical product by a relevant regulatory authority.

As used herein the term "analogue" can refer to any variant that retains sufficient structure and relevant activity to be recognized as being related to the base peptide and to serve a similar function. In some embodiments an analogue contains one or more amino acid substitutions, insertions or deletions. In some embodiments an analogue is a truncated version of the base peptide. In some embodiments additional amino acid sequences have been added to one or the other termini of the base peptide. Such additional sequences may aid in the purification of the peptide, or alter its bioavailability or half-life after administration. In some embodiments the analogue can include non-amino acid additions to the peptide, for example, PEGylation.

The herein disclosed compositions, including pharmaceutical compositions, and formulations may contain water or other solvents, salts, buffers, stabilizers, anti-bacterial or anti-fungal agents, or other excipients as are used in pharmaceutical products. Excipients can include: phenol, for example, 0.5%; added cysteine ≤0.1%; NaOH or acetic acid to adjust pH; and water for injection.

As used herein the term "pharmaceutical composition" refers to a composition that is suitable for use as a drug product, including that it facially meets safety standards as would be required by regulatory authorities such as the Food and Drug Administration or corresponding agencies outside the U.S. This is not meant to necessarily imply any particular level of laboratory or clinical testing to demonstrate safety. Rather it refers to meeting appropriate standards of sterility or being aseptic, and excludes substances that would be considered unacceptable due to the harm or potential harm they could cause the patient (human or veterinary, as appropriate), or the active agents; such exclusion being absolute or based on not exceeding an acceptable concentration or amount. In some embodiments, it can also refer to comprising sufficient quantity of active agent to be expected to produce a physiologic effect.

Some embodiments are repository (or depot) formulations of β-endorphin and ACTH. Such formulations release the peptides over time, prolonging their effective half-life and reducing the number of administrations needed in a course of treatment or other time interval. In some embodiments, the repository formulation contains gelatin, for example 13-19% gelatin, for example 16% gelatin, or any sub-range or individual value therein obtained by steps of 0.5%. Alternatively, a copolymer such as poly(lactic-co-glycolic acid) (PLGA) could be used instead of gelatin. A similar half-life prolonging effect can be obtained by PEGylation of the peptide. In some embodiments polyethylene glycol (PEG) is covalently attached to a terminal C residue added to the sequence of the peptide.

In some embodiments, the ACTH and β-endorphin are co-formulated in a single composition. In other embodiments, the ACTH and β-endorphin are formulated separately in which case they may be administered according to the same schedule, or according to different schedules within a common time interval so that the effects of both overlap within that time interval.

In some embodiments, the formulation is provided in a vial. In other embodiments the formulation is provided in a pre-filled syringe. In some embodiments the formulation contains 80 USP units of ACTH per mL. One mg of ACTH corresponds to about 150 units, based on rat potency testing. In some embodiments, after prolonged use, dosage is tapered off in quantity and/or frequency to avoid adrenal insufficiency, or recurrent symptoms, which can occur upon sudden withdrawal of ACTH.

In various embodiments the mass ratio of ACTH to β-endorphin is in the range of 1:1 to 4:1. In some embodiments the mass ratio of ACTH to β-endorphin is 2:1. In some embodiments a dose contains approximately half the molar amount of β-endorphin as ACTH (a mass ratio of about 2.6:1). In another embodiment, the formulation contains 0.5 to 2 mg/mL of ACTH and 0.1 to 1 mg/mL of β-endorphin.

For most uses, a dosage comprising 40-80 U of ACTH in a repository (or other extended half-life) formulation over a 24-72 hour period is appropriate. In other embodiments, an adult dosage comprises about 0.8-1.2, 0.9-1.1, or 1 mg of ACTH. In some embodiments the combination of ACTH and β-endorphin is administered to resolve exacerbations of the disease, while in on other embodiments the combination is administered as a maintenance therapy. In some embodiments the dosage for maintenance therapy is less than for treating acute exacerbations.

Drug dosages are commonly expressed in units of mg/kg or units/kg, or even simply in mg or units if the therapeutic window is wide enough, largely for convenience. However, drug dosages expressed in units of $mg/m^2$ of body surface area can provide greater precision, as drug exposure scales more closely to the subject's body surface area (BSA) than it does to body weight. This can be particularly useful in choosing pediatric dosages. A widely used formula for calculating BSA in humans is the Mosteller Formula: (BSA $(m^2)=\sqrt{\text{height (cm)} \times \text{weight (kg)}/3600}$, however, other formulae exist, for example, the DuBois & DuBois Formula: (BSA $(m^2)=0.20247 \times \text{Height (m)}^{0.725} \times \text{Weight (kg)}^{0.425}$). They give similar results so that any difference is not material.

The dosage can be administered by subcutaneous or intramuscular injection and can be administered by a healthcare professional (for example, a doctor, a nurse, a physician's assistant, or the like) or by a trained patient, a trained parent of a patient, or other trained non-professional assistant. In some embodiments administration is viewed as taking place under the direction of and at the behest of the prescribing physician. In other embodiments administration is viewed as taking place at the behest of the recipient patient. In all cases administration should be viewed as being carried out in order to receive the benefits attendant to the treatment.

As used herein, the terms "treatment," "treating," and the like refer to obtaining a desired pharmacologic and/or physiologic effect. In some embodiments the effect is therapeutic, i.e., the effect partially or completely cures a disease and/or adverse symptom attributable to the disease, or prevents or reduces the worsening thereof. In some embodiments, treatment is directed at resolving acute exacerbations or flare-ups of the disease. In some embodiments treatment is maintenance therapy directed at preventing or mitigating exacerbations or progression of the disease. In other embodiments the effect is prophylactic, i.e. the effect prevents or reduces the incidence or risk of developing the disease and/or an adverse symptom attributable to the disease. A "clinically effective amount" refers to an amount effective, at dosages and for periods of time necessary, to achieve a desired therapeutic or prophylactic result. The clinically effective amount may vary according to factors such as the disease state, age, sex, weight of the individual, etc. Dosage may be further adjusted based on an individual's initial response to treatment. It is within the skill of a physician or pharmacologist to take such considerations into account, in combination with the disclosures and guidance provided herein, to determine the clinically effective amount for any person in need thereof, The two peptides, β-endorphin and ACTH, bind to all of the melanocortin and opioid receptors bound by any of the peptides derived from POMC, and thus can be used to replicate the activity profile of pituitary extracts. In various embodiments, the herein disclosed compositions and formulations of β-endorphin and ACTH can be used to treat a variety of diseases and disorders currently treated with an ACTH-containing pituitary extract, as described in subsequent paragraphs. A combination of β-endorphin and ACTH can be equally or more effective than the pituitary extracts and provide a more completely defined medicament.

Children with various types of childhood epilepsy that may not respond to the usual seizure medicines can be candidates for treatment. Pituitary extracts comprising ACTH have been used primarily in the treatment of infantile spasm (West syndrome) but have also found to be useful in Lennox-Gastaut syndrome, Landau-Kleffner syndrome, and electrical status epilepticus in sleep. Improvement in seizure control has been seen even in the most difficult-to-control epilepsy after treatment with pituitary extract comprising ACTH. Treatment can also improve the child's developmental status.

It is unclear just how ACTH works to stop seizures. It may work directly on the brain in addition to stimulating the adrenal glands. There is some controversy about whether to use low-dose or high-dose ACTH when treating childhood seizures. No definitive study has yet established one dose as superior. However, a typical dosage would comprise 150 U of ACTH/m$^2$/day, divided into two daily intramuscular injections for two weeks. The dosage is then tapered down over a period of several (for example, 4) weeks. Additionally, patients with infantile spasms exhibit depressed levels of both ACTH and β-endorphin.

Acute exacerbations of multiple sclerosis can be treated. Treatment speeds resolution of the acute exacerbation, but has not been shown to impact the long-term course of the disease. However, the non-steroidogenic immune-modulating activities of ACTH support potential usefulness for long-term treatment of multiple sclerosis. Thus, the present compositions and formulations of β-endorphin and ACTH can be useful for chronic treatment of multiple sclerosis in addition to treating acute exacerbations. In some embodiments, a dosage comprising 80-120 units of ACTH is administered daily by intramuscular or subcutaneous injection for 2-3 weeks, or until the exacerbation resolves.

Acute episodes or exacerbations of rheumatic disorders can be treated, such as psoriatic arthritis, rheumatoid arthritis, including juvenile rheumatoid arthritis, and ankylosing spondylitis. Typically, treatment constitutes short-term adjuvant therapy, but in some cases low dose maintenance therapy can be undertaken.

Collagen disease, such as systemic lupus erythematosus and systemic dermatomyositis (polymyositis) can be treated either to address exacerbations or as maintenance therapy.

In the realm of ophthalmic disease, severe acute and chronic allergic and inflammatory processes involving the eye and its adnexa (for example eyelids, lacrimal glands, and tear ducts) can be treated. Specific conditions treated can include keratitis, iritis, iridocyclitis, diffuse posterior uveitis and choroiditis, optic neuritis, chorioretinitis, and anterior segment inflammation.

In the realm of edema, the herein disclosed compositions and formulations can be used to induce diuresis or remission of proteinuria in the nephrotic syndrome without uremia of the idiopathic type or that due to lupus erythematosus.

The herein disclosed compositions and formulations can also be used to treat dermatologic diseases, such as severe erythema multiforme and Stevens-Johnson syndrome; allergic conditions, such as serum sickness; and respiratory disease, such as symptomatic sarcoidosis.

The herein disclosed compositions and formulations can also be used to treat infectious diseases, including viral diseases, particularly to prevent, reduce, mitigate, or eliminate severe or excessive, pathology-causing, immune responses provoked by the infection. In some embodiments, the severe or excessive immune response comprises an inflammatory reaction, such as inflammation of the lung. In one aspect, inflammation of the lung is thromboinflammatory syndrome. In some embodiments, the severe or excessive immune response is cytokine release syndrome (cytokine storm). In some embodiments, the viral disease is COVID-19.

Thus, some embodiments are methods of treatment in which a composition or formulation comprising ACTH and β-endorphin, or analogues thereof, such as described herein above, are administered to a patient in need thereof. In various embodiments the patient in need thereof has an autoimmune disease, an inflammatory disorder, or an allergic disorder. In some embodiments, the disease to be treated is multiple sclerosis, systemic lupus erythematosus, proteinuria in nephrotic syndrome, polymyositis, symptomatic sarcoidosis, psoriatic arthritis, rheumatoid arthritis, ankylosing spondylitis, or severe acute and chronic allergic or inflammatory processes involving the eye. In some embodiments, the disease to be treated is a neurologic or seizure disorder, including venous types of childhood epilepsy, for example, infantile spasms (West syndrome), Lennox-Gastaut syndrome, Landau-Kleffner syndrome, and electrical status epilepticus in sleep. Corresponding embodiments include use of a composition or formulation comprising ACTH and β-endorphin, or analogues thereof, in the treatment of anyone of these diseases or conditions, and use of ACTH and β-endorphin, or analogues thereof, in the manufacture of a medicament for the treatment of anyone of these diseases or conditions. In some embodiments, the composition or formulation comprising ACTH and β-endorphin, or analogues thereof, is administered intramuscularly or subcutaneously. In various embodiments, the composition or formulation comprising ACTH and β-endorphin, or analogues thereof, is administered twice daily, daily, or every 2nd day.

With respect to each of the foregoing diseases and conditions, there are embodiments for treating the disease or condition comprising administering a clinically effective amount of ACTH and β-endorphin to a person in need thereof. In some embodiments administration occurs twice a day, daily, once every second day, or once every third day.

With respect to the foregoing diseases and disorders that recur episodically, such as multiple sclerosis (such as relapsing-remitting multiple sclerosis) and rheumatic disorders, there are embodiments for preventing or reducing the incidence of recurrence of the disease or disorder comprising administering a clinically effective amount of ACTH and β-endorphin to a person in need thereof.

With respect to the foregoing diseases and disorders with a recognizable prodrome or for which a person is at risk (familial risk, environmental risk, etc.), there are embodiments for preventing development of the disease or disorder comprising administering a clinically effective amount of ACTH and β-endorphin to a person in need thereof.

In some embodiments the patient in need thereof is additionally treated with a superoxide dismutase mimetic. In some embodiments the superoxide dismutase mimetic is Tempol (4-oxypiperidol; 1-λ-oxidanyl-2,2,6,6-tetramethylpiperidin-4-ol). In some embodiments, Tempol is in a separate composition than the ACTH and β-endorphin, or analogues thereof. This allows the Tempol to be administered according to a different schedule and/or different route of administration. In some embodiments Tempol is administered orally. In some embodiments, Tempol is administered topically, sublingually, transrectally, intramuscularly, intravenously, or subcutaneously. In some embodiments the dosage of Tempol is 0.01-1000 mg per day. In some embodiments Tempol is included in the composition or formulation comprising ACTH and β-endorphin, or analogues thereof.

LIST OF PARTICULAR EMBODIMENTS

The following listing of embodiments is illustrative of the variety of embodiments with respect to breadth, combinations and sub-combinations, class of invention, etc., elucidated herein, but is not intended to be an exhaustive enumeration of all embodiments finding support herein.

Embodiment 1. A pharmaceutical composition comprising, β-endorphin and adrenocorticotropic hormone (ACTH) or analogues thereof of either or both.

Embodiment 2. A pharmaceutical composition comprising, two active agents, wherein the active agents consist of β-endorphin and ACTH or analogues thereof.

Embodiment 3. The pharmaceutical composition of Embodiment 1, which does not comprise any pro-opiomelanocortin (POMC)-derived peptides other than β-endorphin and ACTH.

Embodiment 4. A repository formulation comprising the pharmaceutical composition of any one of Embodiments 1 to 3.

Embodiment 5. The repository formulation of Embodiment 4 comprising gelatin.

Embodiment 6. The repository formulation of Embodiment 5 comprising 15-17% gelatin.

Embodiment 7. The composition of any one of Embodiments 1-2, or the formulation of any one of claims 4-6, wherein the β-endorphin has the sequence of human β-endorphin (SEQ ID NO: 1).

Embodiment 8. The composition of any one of Embodiments 1-2, or the formulation of any one of claims 4-6, wherein the β-endorphin has the sequence of bovine β-endorphin (SEQ ID NO: 3).

Embodiment 9. The composition of any one of Embodiments 1-2, or the formulation of any one of claims 4-6, wherein the β-endorphin has the sequence of porcine β-endorphin (SEQ ID NO: 5).

Embodiment 10. The composition of any one of Embodiments 1-2, or the formulation of any one of claims 4-6, wherein the ACTH has the sequence of human ACTH (SEQ ID NO: 2).

Embodiment 11. The composition of any one of Embodiments 1-2, or the formulation of any one of claims 4-6, wherein the ACTH has the sequence of bovine ACTH (SEQ ID NO: 4).

Embodiment 12. The composition of any one of Embodiments 1-2, or the formulation of any one of claims 4-6, wherein the ACTH has the sequence of porcine ACTH (SEQ ID NO: 6 or SEQ ID NO: 7).

Embodiment 13. A method of treating an inflammatory, autoimmune, allergic, or neurologic disease or disorder comprising administering the pharmaceutical composition or formulation of any one of Embodiments 1 to 12.

Embodiment 14. The method of Embodiment 13, wherein the neurologic disorder is infantile spasm, Lennox-Gastaut syndrome, Landau-Kleffner syndrome, or electrical status epilepticus in sleep.

Embodiment 15. The method of Embodiment 13, wherein the inflammatory or autoimmune disease is multiple sclerosis.

Embodiment 16. The method of Embodiment 13, wherein the inflammatory or autoimmune disease is psoriatic arthritis; rheumatoid arthritis, ankylosing spondylitis, systemic lupus erythematosus or systemic dermatomyositis.

Embodiment 17. The method of Embodiment 13, wherein the inflammatory or allergic disorder is an ophthalmic disease.

Embodiment 18. The method of Embodiment 17, wherein the ophthalmic disease is keratitis, iritis, iridocyclitis, diffuse posterior uveitis and choroiditis, optic neuritis, chorioretinitis, or anterior segment inflammation.

Embodiment 19. The method of Embodiment 13, wherein the inflammatory or allergic disorder is edema, severe erythema multiforme, Stevens-Johnson syndrome, serum sickness, or symptomatic sarcoidosis.

Embodiment 20. The method of any one of Embodiments 13-19, further comprising administration of Tempol.

Embodiment 21. A syringe, pre-filled with the formulation of any one of Embodiments 4 to 12.

Embodiment 22. The use of the composition of any one of Embodiments 1-2, or the formulation of any one of claims 4-6, for the treatment an inflammatory, autoimmune, allergic, infectious, or neurologic disease or disorder.

Embodiment 23. A method of treating an inflammatory, autoimmune, allergic, infectious, or neurologic disease or disorder comprising administering a clinically effective amount of adrenocorticotropic hormone (ACTH) and β-endorphin, or analogues thereof of either or both, to a person in need thereof.

Embodiment 24. The method of Embodiment 23, wherein the disease or disorder is infantile spasms, multiple sclerosis, a rheumatic disorder, a collagen disease, a dermatologic disease, an allergic disorder, an ophthalmic disease, a respiratory disease, or an edematous disorder.

Embodiment 25, The method of Embodiment 24, wherein the rheumatic disorder is rheumatoid arthritis, juvenile rheumatoid arthritis, psoriatic arthritis, or ankylosing spondylitis.

Embodiment 26. The method of Embodiment 24, wherein the collagen disease is systemic lupus erythematosus, or systemic dermatomyositis. (Systemic dermatomyositis is also known as polymyositis).

Embodiment 27, The method of Embodiment 24, wherein the dermatologic disease is severe erythema multiforme or Stevens-Johnson syndrome.

Embodiment 28. The method of Embodiment 24, wherein the allergic disorder is serum sickness.

Embodiment 29. The method of Embodiment 24, wherein the ophthalmic disease is a severe acute or chronic allergic or inflammatory process involving an eye or its adnexa.

Embodiment 30. The method of Embodiment 29, wherein the allergic or inflammatory process is keratitis, iritis, iridocyclitis, diffuse posterior uveitis or choroiditis, optic neuritis, choriorentinitis, or anterior segment inflammation.

Embodiment 31. The method of Embodiment 24, wherein the respiratory disease is symptomatic sarcoidosis.

Embodiment 32, The method of Embodiment 24, wherein the edematous disorder is proteinuria in nephrotic syndrome.

Embodiment 33. The method of Embodiment 23, wherein the neurologic disease or disorder is childhood epilepsy, infantile spasms (West syndrome), Lennox-Gastaut syndrome, Landau-Kleffner syndrome, or electrical status epilepticus in sleep.

Embodiment 34. The method of any one of Embodiments 23-33, wherein treating comprises mitigating or resolving an acute exacerbation of the disease.

Embodiment 35. The method of any one of Embodiments 23-33, wherein treating comprises maintenance therapy, whereby incidences or severity of exacerbations of the disease is reduced.

Embodiment 36. The method of Embodiment 35, wherein the disease in relapsing-remitting multiple sclerosis and the incidence or severity of relapses is reduced.

Embodiment 37. The method of Embodiment 23, wherein the infectious disease is a viral disease comprising an excessive or severe immune response.

Embodiment 38. The method of Embodiment 27, wherein the infectious disease is COVID-19.

Embodiment 39. The method of any one of Embodiments 23-33 or 37-38, wherein the treatment is prophylactic.

Embodiment 40. The method of Embodiment 39, wherein the disease or disorder has a recognizable prodrome.

Embodiment 41. The method of Embodiment 39, wherein the person in need thereof has an elevated risk of developing the disease or severe symptoms thereof.

Embodiment 42. The method of Embodiment 41, wherein the risk is familial or environmental.

Embodiment 43. The method of Embodiment 23, wherein the person in need thereof has a family history of multiple sclerosis, and the treatment is prophylactic.

Embodiment 44. The method of any one of Embodiments 23-43 comprising administering 40-120 units of ACTH.

Embodiment 45. The method of any one of Embodiments 23-43, comprising administering 0.8-1.2 mg of ACTH.

Embodiment 46. The method of Embodiment 45, comprising administering about 1 mg of ACTH.

Embodiment 47. The method of one of Embodiments 23-46, wherein the mass ratio of ACTH:β-endorphin is 2:1.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the methods of treating any of the above disorders.

Example 1

Effect of β-Endorphin and ACTH in an Animal Model of Infantile Spasms

The Ts65Dn mouse was initially developed as a model of Down's syndrome, but shows spontaneous spike-and-wave discharges (Cortez, M. A., et al., *Pediatric Research* 65(5): 499-503 (2009). Gamma-aminobutyric acid B (GABA$_B$R) agonists, such as baclofen and γ-butyrolactone, induce acute epileptic extensor spasms (AEES) associated with epileptiform polyspike bursts and an electrodecremental response on the EEG. The GABA$_B$R agonist-treated Ts65Dn mouse shows the unique clinical, electrographic, and pharmacologic signature of infantile spasms and represents a valid, acute model of this disorder. Rodent (but not porcine) ACTH (SEQ ID NO: 9) can significantly reduce AEES.

Cohorts of TS65Dn mice are administered a GABA$_B$R agonist and treated with a vehicle control, murine ACTH$_{1-24}$, murine ACTH$_{1-39}$, murine β-endorphin (SEQ ID NO: 8), murine ACTH$_{1-24}$ plus β-endorphin, or murine ACTH$_{1-39}$ plus murine β-endorphin and evaluated for the reduction in the number of AEES and of electrodecremental response.

Example 2

Effect of β-Endorphin and ACTH in a Murine Model of Relapsing-Remitting Multiple Sclerosis Experimental autoimmune encephalitis (EAE) is the standard model used to test potential therapies for multiple sclerosis. One particular presentation of EAE is the SJL/J mouse sensitized with synthetic myelin basic protein 139-151 peptide (PLP$_{139-151}$), which induces a relapsing-remitting form of the disease (RR-EAE). H.P. Acthar Gel® (Acthar) has been shown to reduce mean clinical score during relapse and cumulative disease burden in comparison to placebo as well as ameliorating inflammation/demyelination in the spinal cord. Acthar treatment also suppresses ex vivo myelin peptide induced CD4$^+$ T cell proliferation (Cusick et al., *Autoimmunity* 48(4):222-230 (2015).

RR-EAE is induced according to standard protocol. Briefly, SJL/J mice are sensitized by subcutaneous injection of with PLP$_{139-151}$ in complete Freund's adjuvant (CFA), followed by intravenous injections of *Bordetella pertussis* toxin. The mice are then randomized into the following treatment arms using a repository formulation: vehicle control, ACTH, β-endorphin, and ACTH plus β-endorphin; with comparison of human sequence to either porcine or murine sequence. In separate studies treatment is begun immediately upon relapse and five days after the onset of relapse. The mice are monitored daily for weight and clinical signs. Clinical scoring uses the scale: 0, no clinical signs; 1, loss of tail tonicity; 2, presents with mild hind leg paralysis with no obvious gait disturbance; 3, mild leg paralysis with gait disturbance and paralysis; 4, hind legs are paralyzed; and 5, moribund or dead. Histology is performed on spinal cords harvested after death by euthanasia and scored for inflammation and demyelination.

ACTH plus β-endorphin dampens RR-EAE and ameliorates inflammation and demyelination to a greater extent that ACTH alone.

Example 3

Effect of β-Endorphin and ACTH in EAE, a Murine Model of Relapsing-Remitting Multiple Sclerosis The effect of administration of two dosages of ACTH and β-endorphin on severity and relapse in EAE was evaluated. EAE was induced in SJL mice by $PLP_{139-151}$/CFA immunization on Day 0. Treatment was late therapeutic, starting on Day 20 after immunization for each mouse. Mice were observed through the end of the study, Day 42 after immunization. Four groups of 20 mice each received one of the following treatments: vehicle (a negative control); 10 mg/kg oral prednisolone daily (reference treatment); 32 µg ACTH+ 16 µg endorphin by subcutaneous injection, every 2nd day (low dose); or 64 µg ACTH+32 µg β-endorphin by subcutaneous injection, every 2nd day (high dose).

EAE Induction

Mice were injected subcutaneously at four sites in the back with emulsion containing $PLP_{139-151}$ (native sequence) from HOOKE KIT™ $PLP_{139-151}$/CFA Emulsion, catalog number EK-0120 (Hooke Laboratories, Lawrence Mass.). Two sites of injection were in the upper back approximately 1 cm caudal of the neck line. The other two sites were in the lower back approximately 2 cm cranial of the base of the tail. The injection volume was 0.05 mL at each site. Even without treatment, most mice recover spontaneously after the first wave of disease. In the SJL model, EAE develops 10-15 days after immunization in 90-100% of immunized mice. The first wave of EAE lasts several days and most mice fully or almost fully recover from this first wave. After a disease-free period, which can last from one day to several months, most mice relapse. During the first 5-7 weeks after immunization, 50-100% of mice will develop a relapse. Each wave of paralysis results in body weight loss at onset, most of which is regained at recovery from the wave. The greatest weight loss is during the first wave of EAE. During the chronic phase of disease, the average EAE body weight is relatively stable, with normal slow increase with age. Since individual mice experience relapses at different times, only a few mice in each group are acutely sick at any given time after the first wave of EAE. Therefore, significant differences in relative body weight between groups are often not found after the first wave of disease in this model. In the vehicle treated group, disease developed as expected for this model. Five (5) mice were euthanized on Day 30 for analysis. Relapse occurred in 7 out of the 15 remaining mice, which were followed to Day 42, with typical course and severity of disease.

Treatment

100 EAE induced mice were initially considered a single group and were scored daily starting on Day 9 after immunization. On Day 20, mice were assigned to the experimental groups in a balanced manner to achieve groups with similar times of EAE onset, similar maximum EAE score and similar scores at the time of enrollment into treatment (see Table 3). The remaining mice, which developed EAE last, or which developed unusual signs of EAE such as head tilting, were not assigned to any treatment group.

TABLE 3

| | | | Treatment regimen | | | | |
|---|---|---|---|---|---|---|---|
| Group | # of Animals | Treatment | Dose | Route | Frequency | Volume | Purpose |
| 1 | 20 | Vehicle | — | s.c. | Q2D | 0.1 mL | Negative control |
| 2 | 20 | Low Dose | ACTH: 32 µg β-end: 16 µg | s.c. | Q2D | 0.1 mL | Test |
| 3 | 20 | High Dose | ACTH: 64 µg B-end: 32 µg | s.c. | Q2D | 0.1 mL | Test |
| 4 | 20 | Prednisolone | 10 mg/kg | p.o. | QD | 10 mL/kg | Reference |

Vehicle was 16% gelatin from porcine skin (Sigma G2500-100G) prepared by dissolution in 60° C. sterile water with pH adjusted with 1 N NaOH to be 6.3 to 6.6. For the high dose treatment, porcine ACTH and porcine β-endorphin were dissolved in vehicle by heating to 80-90° C. for 20 minutes and then cooling to 60-70° C. followed by addition of ACTH and β-endorphin powder to achieve a concentration of 0.64 and 0.32 mg/ml solution, respectively, and stirring at 50-70° C. for 20 minutes; pH was between 6 and 7. For the low dose treatment this solution was diluted 1:2 with vehicle.

Treatment started on the day of group assignment (Day 20 after immunization). This was the time of the expected end of the first wave of EAE and before relapses were expected to begin. Treatment continued through Day 41. EAE score was determined daily by a person unaware of both treatment and of previous scores for each mouse. Weight was measured 3 times a week. Five mice in each group were euthanized on day 30 and the fifteen remaining mice euthanized at the end of the study (Day 42). Histological and immunohistological analyses were performed on tissue collected from the euthanized mice.

TABLE 4

EAE scoring criteria

Score Clinical observations

0. No obvious changes in motor functions of the mouse in comparison to non-immunized mice. When picked up by the tail, the tail has tension and is erect. Hind legs are usually spread apart. When the mouse is walking, there is no gait or head tilting.
1. Limp tail. When the mouse is picked up by the tail, instead of being erect, the whole tail drapes over your finger.
2. Limp tail and weakness of hind legs. When mouse is picked up by tail, legs are not spread apart, but held closer together. When the mouse is observed when walking, it has a clearly apparent wobbly walk.
3. Limp tail and complete paralysis of hind legs (most common).
   OR
   Limp tail with paralysis of one front and one hind leg.
   OR
   ALL of:
   Severe head tilting,
   Walking only along the edges of the cage,
   Pushing against the cage wall,
   Spinning when picked up by the tail.
4. Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, score of 5 is entered for that mouse for the rest of the experiment.
5. Complete hind and complete front leg paralysis, no movement around the cage. OR Mouse is spontaneously rolling in the cage. OR Mouse is found dead due to paralysis.

In-between scores were assigned when the clinical signs fell between defined scores.

Figure 2:
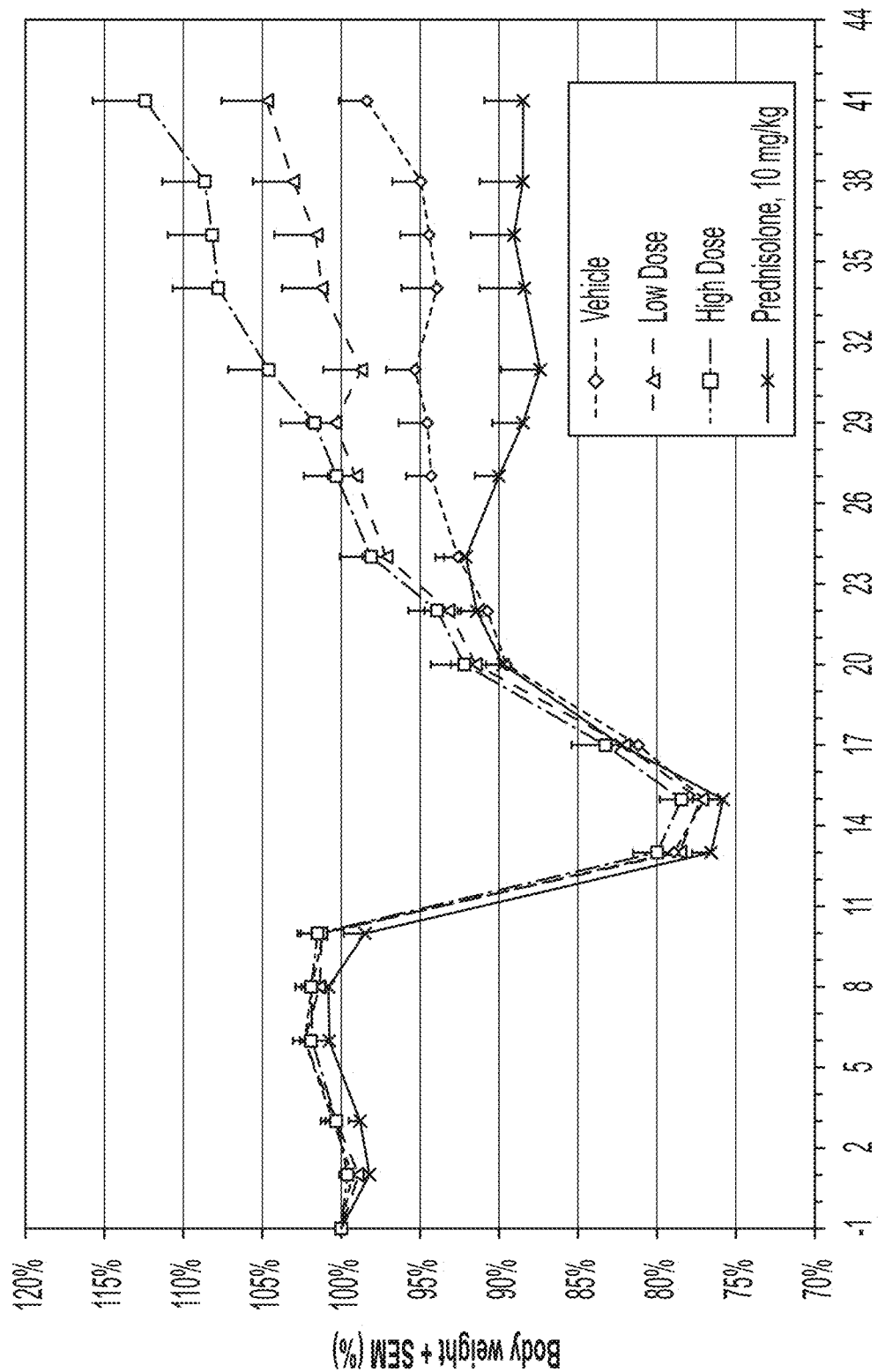
FIG. 2 depicts the change in body weight over the course of the study for each of the four groups: Vehicle (diamond), ACTH+β-endorphin–Low dose (triangle), ACTH+β-endorphin–High dose (square), and prednisolone (reference treatment; x). In this study low dose was 32 μg ACTH, 16 μg β-endorphin, and high dose was 64 μg ACTH, 32 μg β-endorphin.

Statistical analyses of the clinical findings are presented in Table 5 and of the histological and immunohistological finding are presented in Table 6. Overall disease severity in this experiment, as reflected in the mean maximal score (MMS), was moderate, limiting the statistical power of clinical observations. Nonetheless the MMS for high dose treatment was borderline statistically significant. Mean clinical score was also recorded over the course of the study (see FIG. 1) showing the clear benefit of the High dose treatment and the more moderate benefit of the Low dose and Reference treatments, all as compared to vehicle. Weight gain is another signal of clinical improvement. Both the low and high dose groups exhibited weight gain versus the vehicle control, with the high dose group showing clear statistical significance. In contrast, the prednisolone treatment group exhibited a statistically significant loss of weight versus the vehicle control emphasizing the marginal value of this treatment and indicating that even the low dose treatment with ACTH and β-endorphin provided a real improvement (see FIG. 2). Additionally, there was a trend toward reduced incidence of relapse in both the high and low dose groups that was greater than for the prednisolone treatment.

The histological analyses revealed a statistically significant reduction in inflammation and inflammatory infiltrates by both the low and high dose treatments, as evidenced by a reduction in the number of inflammatory foci as compared to the vehicle control. Similarly, both the low and high dose treatments led to a statistically significant reduction in demyelination, as evidenced by anti-myelin basic protein staining score. (Demyelination score: 0-<5% demyelinated area, 1-5-20% demyelinated area, 2-21-40% demyelinated area, 3-41-60% demyelinated area, 4-61-80% demyelinated area, and 5-81-100% demyelinated area,) Microglial activation, another indicator of inflammation, quantitated as the area of anti-Iba1 staining, and gliosis (scarring), quantitated as the area of anti-GFAP staining were also both statistically significantly reduced, as compared to the vehicle control, by both the high and low dose treatment with ACTH and β-endorphin. In contrast, prednisolone treatment showed only at best a trend to reduction of inflammation and demyelination (and a higher level of gliosis), with none of these values approaching statistical significance. Collectively, these results indicate that treatment with ACTH and β-endorphin has greater efficacy in reducing EAE than prednisolone, especially at the higher of the two dosages tested, and support an expectation of similar beneficial effect in treating multiple sclerosis.

TABLE 5

Statistical analysis of clinical findings

| | All mice | | | | | Mice not terminated on Day 30[||] | | | | | |
|---|---|---|---|---|---|---|---|---|---|---|---|
| Treatment | Mean day of onset ± SD | MMS of first wave ± SD | Day 20 score ± SD | Incidence of relapse[†] | p value | MMS of relapse period ± SD (Days 25-42)[‡] | p value | End score ± SD | p value | End % body weight ± SD | p value |
| Vehicle | 11.9 ± 0.8 | 3.30 ± 0.55 | 2.08 ± 0.59 | 46.7% | | 2.50 ± 0.87 | | 1.73 ± 1.02 | | 98.4% ± 6.8% | |
| Low Dose | 11.9 ± 0.7 | 3.25 ± 0.47 | 2.10 ± 0.53 | 20.0% | 0.1174 | 2.10 ± 0.57 | 0.2014 | 1.30 ± 0.86 | 0.1658 | 104.8% ± 11.0% | 0.0647 ** |

TABLE 5-continued

Statistical analysis of clinical findings

| | All mice | | | | | Mice not terminated on Day 30[‖] | | | | | |
| --- | --- | --- | --- | --- | --- | --- | --- | --- | --- | --- | --- |
| | | | | | | MMS of | | | | | |
| Treatment | Mean day of onset ± SD | MMS of first wave ± SD | Day 20 score ± SD | Incidence of relapse[†] | p value | relapse period ± SD (Days 25-42)[‡] | p value | End score ± SD | p value | End % body weight ± SD | p value |
| High Dose | 12.0 ± 0.9 | 3.28 ± 0.53 | 2.05 ± 0.69 | 20.0% | 0.1174 | 1.77 ± 1.02 | 0.0502 ** | 1.10 ± 1.00 | 0.1060 | 112.5% ± 12.9% | 0.0009 * |
| Prednisolone, 10 mg/kg | 11.9 ± 0.7 | 3.33 ± 0.54 | 2.05 ± 0.65 | 33.3% | 0.4552 | 2.07 ± 1.10 | 0.2530 | 1.47 ± 1.04 | 0.3665 | 88.6% ± 9.3% | 0.0026 * |

* $p < 0.05$ vs. vehicle
** $p < 0.10$ vs. vehicle
[†]Mice that relapsed as a proportion of surviving mice that developed the first wave of EAE
[‡]Calculated for all mice in the group
[‖]That is, mice followed until Day 42
Disease relapse compared using chi-square test
MMSs compared using Wilcoxon's non-parametric test
End EAE scores compared using Wilcoxon's non-parametric test
Change in body weight at the end of the study compared using two-tailed Student's t-test

TABLE 6

Statistical analysis of histological and immunohistological findings

| Treatment | Inflammatory foci/section ± SD | p value | Demyelination (anti-MBP) ± SD | p value | Iba1 ± SD (% of area) | p value | GFAP ± SD (% of area) | p value |
| --- | --- | --- | --- | --- | --- | --- | --- | --- |
| Vehicle | 4.3 ± 2.8 | | 1.1 ± 0.6 | | 4.7 ± 1.6 | | 12.5 ± 1.8 | |
| Low Dose | 1.6 ± 1.0 | 0.0014* | 0.5 ± 0.4 | 0.0084* | 2.4 ± 0.5 | <0.0001* | 11.0 ± 1.8 | 0.0288* |
| High Dose | 1.2 ± 1.1 | 0.0004* | 0.4 ± 0.4 | 0.0013* | 2.3 ± 0.5 | <0.0001* | 9.0 ± 1.2 | <0.0001* |
| Prednisolone, 10 mg/kg | 3.8 ± 2.4 | 0.6134 | 0.9 ± 0.6 | 0.3777 | 4.0 ± 1.2 | 0.1538 | 13.3 ± 2.0 | 0.2819 |

*$p < 0.05$ vs. vehicle
Number of inflammatory foci were compared using 2-tailed Student's t-test
Demyelination (anti-MBP) was compared using Wilcoxon's non-parametric test
Apoptosis (number of apoptotic cells) was compared using 2-tailed Student's t-test
Iba1 and GFAP (% of total spinal cord area) compared using 2-tailed Student's t-test Example 4

Effect of ACTH and β-Endorphin in EAE, a Therapeutic Murine Model of Relapsing-Remitting Multiple Sclerosis Example 3 showed ACTH and β-endorphin treatment of EAE produced strong efficacy in histologic analysis and suggested dose responsiveness for clinical readouts (particularly incidence of relapse). To further explore the effect of dosage, the model was repeated, essentially as described in Example 3, using greater doses, specifically 53 μg of ACTH+27 μg of β-endorphin (low dose), and 128 βg of ACTH+64 μg of β-endorphin (high dose). Additionally FTY720 (fingolimod, an FDA-approved drug for the treatment of multiple sclerosis) was used as a reference (positive control) treatment instead of prednisolone, which had not shown strong efficacy in Example 3. FTY720 is one of the most efficacious drugs in both EAE and MS. Immunization was on Day 0, treatment started on Day 20, and the mice were observed through Day 42. An overview of the treatment regimen is provided in Table 7.

TABLE 7

Treatment regimen

| Group | # of Animals | Treatment | Dose | Route | Frequency | Volume | Purpose |
| --- | --- | --- | --- | --- | --- | --- | --- |
| 1 | 30 | Vehicle | — | s.c. | Q2D | 0.1 mL | Negative control |
| 2 | 30 | Low Dose | ACTH: 53 μg β-end: 27 μg | s.c. | Q2D | 0.1 mL | Test |
| 3 | 30 | High Dose | ACTH: 128 μg β-end: 64 μg | s.c. | Q2D | 0.1 mL | Test |
| 4 | 9 | FTY720 | 1 mg/kg | p.o. | QD | 5 mL/kg | Reference |

Figure 3:
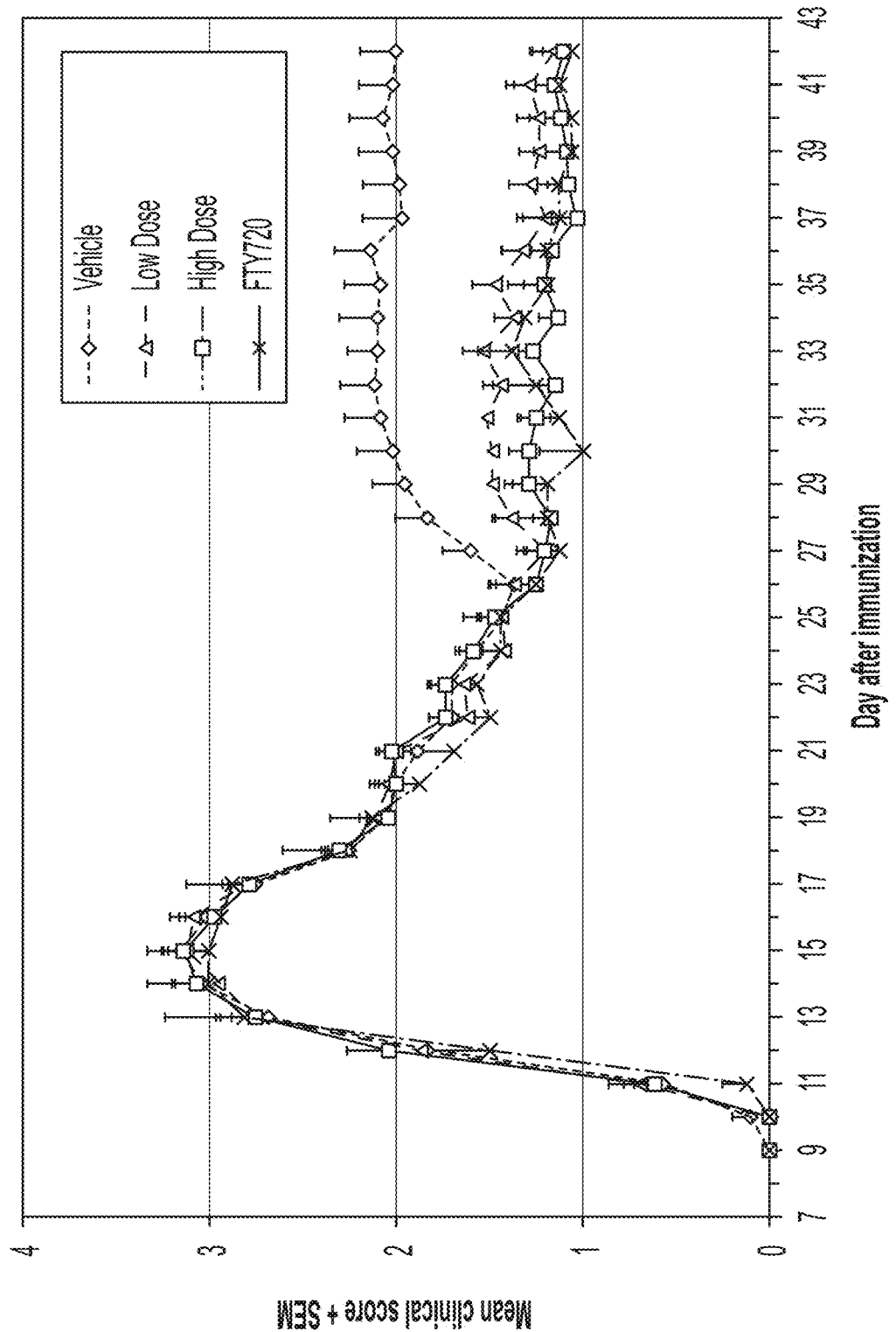
FIG. 3 depicts the change in EAE severity (mean clinical score) over the course of the study for each of the four groups: Vehicle (diamond), ACTH+β-endorphin–Low dose (triangle), ACTH+β-endorphin–High dose (square), and FTY720 (reference treatment; x). In this study low dose was 53 μg ACTH, 27 μg β-endorphin, and high dose was 128 μg ACTH, 64 μg β-endorphin.
Figure 4:
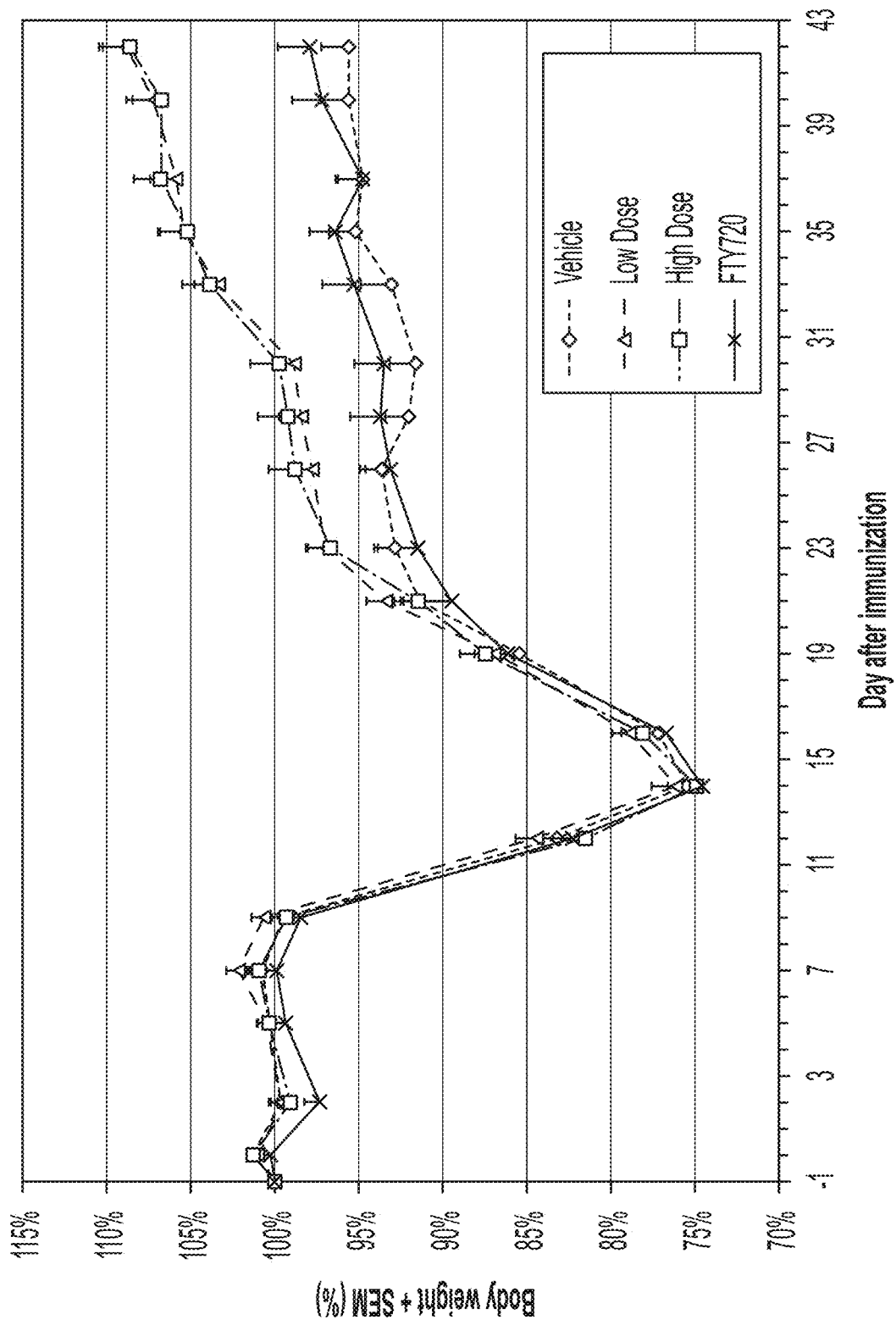
FIG. 4 depicts the change in body weight over the course of the study for each of the four groups: Vehicle (diamond), ACTH+β-endorphin–Low dose (triangle), ACTH+β-endorphin–High dose (square), and FTY720 (reference treatment; x). In this study low dose was 53 μg ACTH, 27 μg β-endorphin, and high dose was 128 μg ACTH, 64 μg β-endorphin.

EAE severity (mean clinical score) over the course of the study (see FIG. 3) shows a clear separation of vehicle from the three treatment groups starting at Day 27 as the mice in the vehicle group began to relapse. Clinical results are summarized in Table 8. Readouts are End score, End body weight (% of starting weight), Incidence of relapse, and Mean maximal score (MMS) in the relapse period. All clinical readouts of efficacy were similar between the FTY720 and Test groups. Both test treatments treatment showed improvement over the vehicle control for all readouts, with statistical significance of p<0.05 versus vehicle. Both test treatments allowed for modest weight gain during the trial (see FIG. 4) and End body weight for the High Dose group attained statistical significance (p=0.0023) versus the reference treatment as well. (End weight was likely statistically significant in the low dose group, but this was not analyzed). In this model higher body weight is an indication of efficacy. The reference treatment showed statistically significant improvement versus vehicle for all readouts except End weight.

Incidence of relapses is the primary and most important readout in this model. Both the High dose and Low dose test groups significantly reduced relapses, with the high dose completely preventing new relapses. It is rare to see any treatment other than FTY720 completely suppress relapses in this model. One of the thirty mice in the High Dose group relapsed on the day treatment started, and it had substantially recovered by the end of the study. One of the nine mice in the reference treatment (FTY720) group also relapsed on the day treatment started, and also had substantially recovered by the end of the study.

Figure 5:
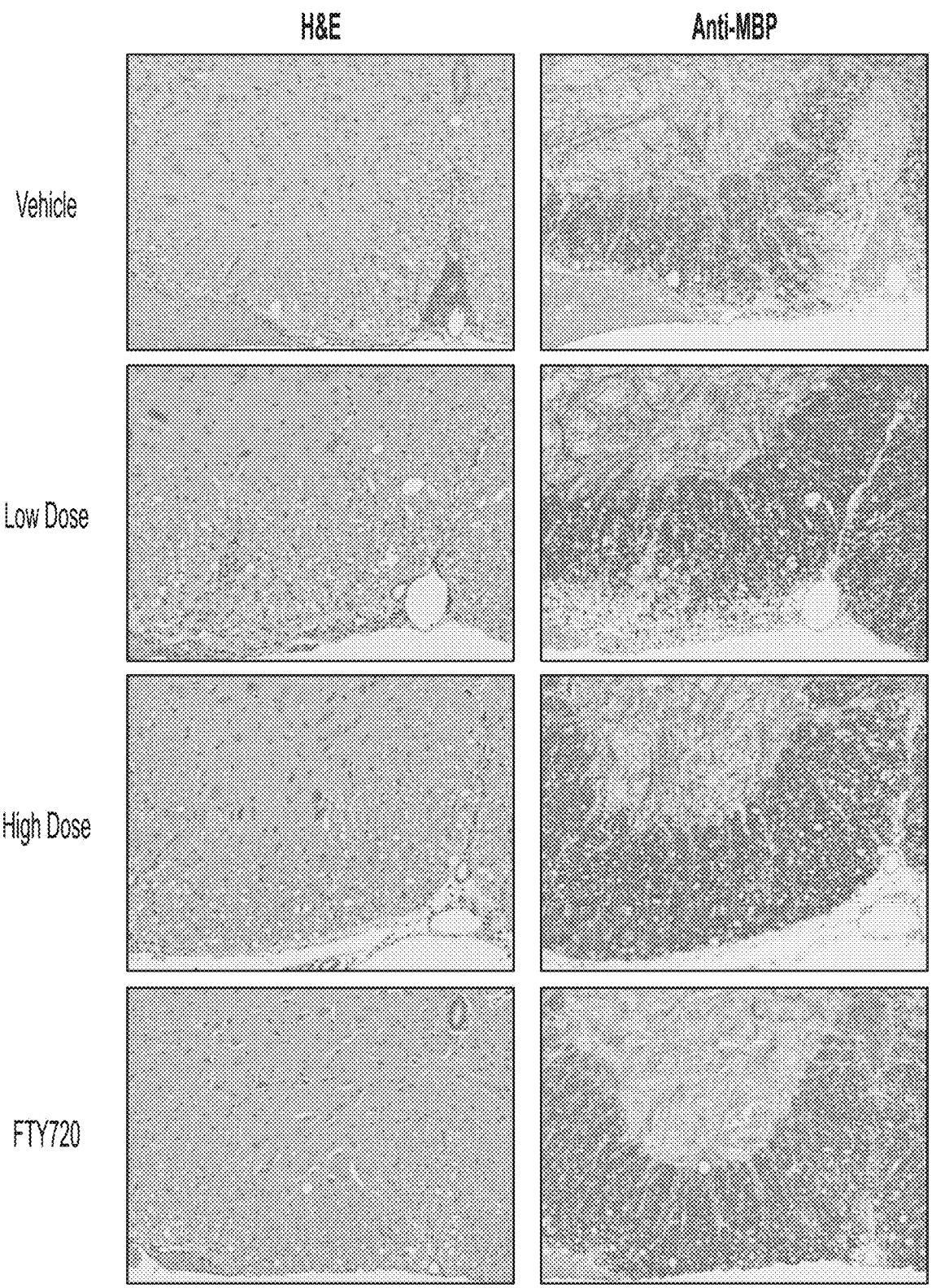
FIG. 5 presents representative micrographs of sections of spines stained with H&E and anti-MBP (myelin basic protein) for each of the four groups: Vehicle, ACTH+β-endorphin–Low dose, ACTH+β-endorphin–High dose, and FTY720 (reference treatment). In this study low dose was 53 μg ACTH, 27 μg β-endorphin, and high dose was 128 μg ACTH, 64 μg β-endorphin.

Histological analysis confirmed the clinical findings (Table 9). Histologic readouts were inflammatory foci per section, demyelination (based on anti-myelin basic protein (MBP) staining), and apoptotic cells per section. Significantly fewer inflammatory infiltrates were observed in the spinal cords of test group mice vs. vehicle (see FIG. 5); the reduction was dose dependent. A low number of inflammatory infiltrates confirms absence of both clinical and subclinical inflammation in the CNS. Histological findings in the high dose test group were generally similar to the FTY720 reference group. However, demyelination for the High dose test group was also improved over the FTY720 to a statistically significant degree (p=0.0055).

These results show that the combination of ACTH and β-endorphin is a very effective treatment for EAE, reducing inflammation and demyelination, preventing or reducing the incidence of relapse, and improving symptomology.

TABLE 8

Statistical analysis of clinical findings

| Treatment | End score ± SD | p value | End % body weight ± SD | p value | Incidence of relapse* | p value | MMS of relapse period ± SD (Days 20-42)** | p value |
|---|---|---|---|---|---|---|---|---|
| Vehicle | 2.00 ± 1.05 | | 95.6% ± 9.1% | | 53.3% | | 2.67 ± 0.87 | |
| Low Dose | 1.15 ± 0.68 | 0.0004[1] | 108.8% ± 9.0% | <0.0001[1] | 16.7% | 0.0024[1] | 2.22 ± 0.49 | 0.0159[1] |
| High Dose | 1.10 ± 0.62 | <0.0001[1] 0.8245[2] | 108.6% ± 8.8% | <0.0001[1] 0.0023[2] | 3.3% | <0.0001[1] 0.3500[2] | 2.13 ± 0.47 | 0.0043[1] 0.4508[2] |
| FTY720 | 1.06 ± 0.62 | 0.0109 | 97.65 ± 5.3% | 0.4896 | 12.5% | 0.0289 | 1.94 ± 0.50 | 0.0215 |

*Mice that relapsed as a proportion of surviving mice that developed the first wave of EAE
**Calculated for all mice in the group
[1]Compared to vehicle
[2]Compared to FTY720, 1 mg/kg

TABLE 9

Statistical analysis histological findings

| Treatment | Inflammatory foci/section ± SD | p value | Demyelination (anti-MBP) ± SD | p value | Apoptotic cells/section ± SD | p value |
|---|---|---|---|---|---|---|
| Vehicle | 4.4 ± 1.7 | | 0.4 ± 0.5 | | 0.6 ± 0.7 | |
| Low Dose | 1.2 ± 1.0 | <0.0001 | 0.0 ± 0.1 | <0.0001 | 0.2 ± 0.2 | 0.0045 |
| High Dose | 0.6 ± 0.7 | <0.0001[1] 0.6340[2] | 0.0 ± 0.0 | <0.0001[1] 0.0055[2] | 0.1 ± 0.2 | 0.0003[1] 0.2095[2] |
| FTY720 | 0.5 ± 0.4 | <0.0001 | 0.1 ± 0.2 | 0.0791[3] | 0.3 ± 0.4 | 0.1469 |

[1]Compared to vehicle
[2]Compared to FTY720, 1 mg/kg
[3]Significant compared to vehicle if the criterion for statistical significance is set at p < 0.10 instead of p < 0.05

Example 5

Effect of ACTH and β-Endorphin in EAE, a Prophylactic Murine Model of Multiple Sclerosis The efficacy of the combination of ACTH and β-endorphin was also tested in a prophylactic model of EAE. In contrast with the therapeutic model used above, in which treatment is initiated only after EAE onset and recovery from the first wave of the disease, in the prophylactic model, treatment is initiated at the time of immunization and the mice are followed for only 3 weeks. Additionally, pertussis toxin (PTX) is used as an additional adjuvant in the immunization, producing a more sever first wave of disease with slower recovery.

Mice were injected subcutaneously at four sites in the back with 0.05 mL of the emulsion component of HOOKE KIT™ PLP139-151/CFA Emulsion PTX (catalog number EK-2120; Hooke Laboratories, Lawrence Mass.). Two sites of injection were in the upper back approximately 1 cm caudal of the neck line. The other two sites were in the lower back approximately 2 cm cranial of the base of the tail. Two hours later the pertussis toxin component of the kit was administered intraperitoneally. A 30 ng dose of PTX was used to attain optimal disease severity. Mice were administered vehicle or 128 μg ACTH+64 μg β-endorphin by subcutaneous injection every 2nd day, as a negative control and test treatment, respectively. As reference treatment (positive control) mice received 3 mg/kg FTY720 daily by oral administration. There were 12 mice in each of these three groups. The vehicle and test treatment groups were dosed from Day 0 through Day 18 (the last dose in the test treatment group was 88 μg ACTH+44 μg β-endorphin due to lab mishap). The reference treatment group was dosed from Day 0 through Day 19. Clinical scoring was as presented in Table 4 (above) beginning on Day 7 and continuing through Day 20.

Figure 6:
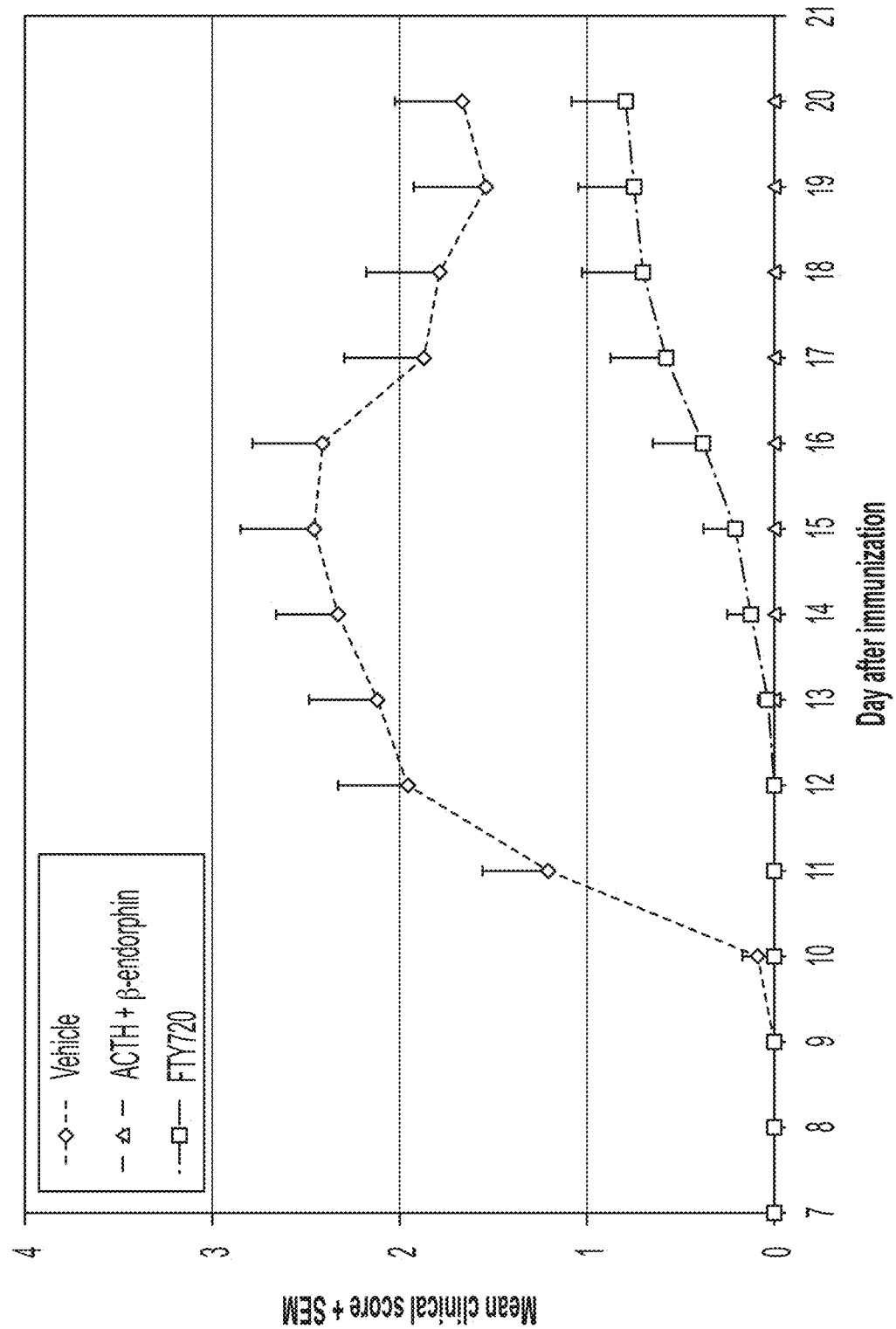
FIG. 6 depicts the change in EAE severity (mean clinical score) over the course of the study for each of the three groups: Vehicle (diamond), ACTH+β-endorphin (triangle), and FTY720 (reference treatment; square). In this study low dose was 53 μg ACTH, 27 μg β-endorphin, and high dose was 128 μg ACTH, 64 μg β-endorphin.
Figure 7:
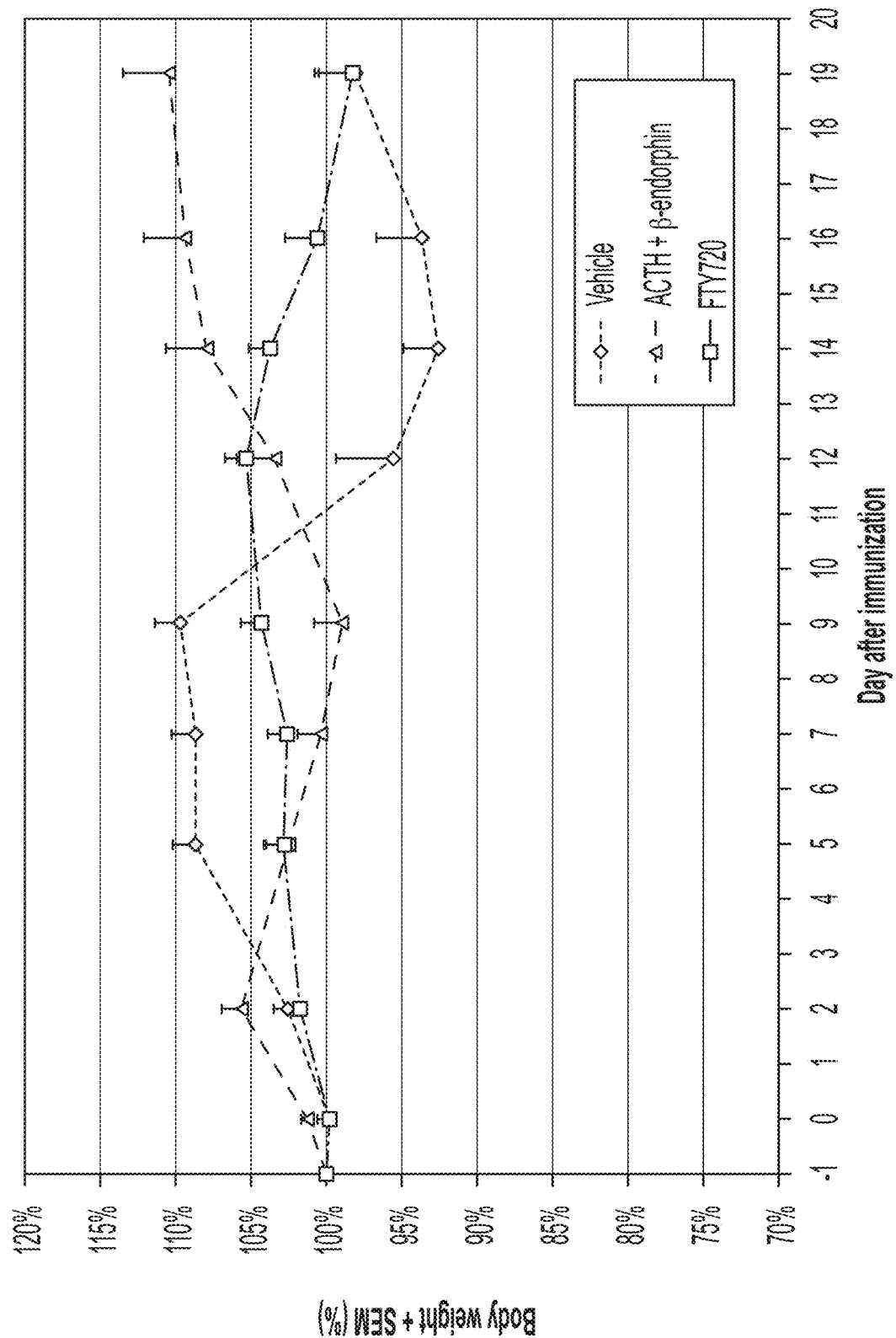
FIG. 7 depicts the change in body weight over the course of the study for each of the three groups: Vehicle (diamond), ACTH+β-endorphin (triangle), and FTY720 (reference treatment; square). In this study the test dose was 128 μg ACTH, 64 μg β-endorphin.

AE severity (mean clinical score) over the course of the study (see FIG. 6) shows a clear separation of vehicle from the two treatment groups starting at Day 10 as the mice in the vehicle group began to exhibit symptoms of the disease. The clinical findings are summarized in Table 10. Change in body weight over the course of the study is shown in FIG. 7. FTY720 was efficacious (as expected for a positive control), with EAE incidence, onset, and MMS all significantly improved vs. vehicle. (End score for FTY720 was also statistically significant if the criterion for statistical significance is set at p<0.10 instead of p<0.05). These are typical results for FTY720 in this model. The combination of ACTH and β-endorphin completely suppressed EAE development. That is, no mice in this group developed EAE. Not only were all clinical readouts significantly improved compared to the Vehicle group but, remarkably, they were significantly improved compared to the Reference treatment group. This is a very unusual result, especially in light of the high dose of FTY720 used. In past experience with this model, neither COPAXONE® (glatiramer acetate injection) nor TECFIDERA® (dimethyl fumarate) completely suppressed development of EAE. These results show that the combination of ACTH and β-endorphin is surprisingly effective treatment for EAE, capable of preventing the development of clinically observable disease.

Example 6

Prophylactic Treatment of COVID-19

A patient with early symptoms COVID-19, or an asymptomatic patient with a positive SARS-CoV-2 infection test, is administered a composition of ACTH and β-endorphin, with a mass ratio of ACTH:β-endorphin of 2:1, by daily intramuscular or subcutaneous injection at a dosage of 80-120 units of ACTH. Treatment is continued for 2-3 weeks or until the patient tests negative for SARS-CoV-2 infection Severe inflammatory symptoms and cytokine release syndrome do not emerge, or are reduced in duration and/or severity as compared to untreated patients.

Example 7

Therapeutic Treatment of COVID-19

A patient with worsening symptoms of COVID-19 and a positive SARS-CoV-2 infection test is administered a composition of ACTH and β-endorphin, with a mass ratio of ACTH:β-endorphin of 2:1, by once or twice daily intramuscular injection for a total daily dosage of 80-150 units ACTH/$m^2$. Treatment is continued until any symptoms of cytokine release syndrome or other inflammatory response abate. The dosage may be tapered down as symptoms lessen according to the judgement of the treating physician.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of

TABLE 10

Statistical analysis of clinical findings

| Treatment | EAE incidence (%) | p value | Median day of onset (all mice) | p value | MMS ± SD | p value | End score ± SD | p value | End % body weight ± SD | p value |
|---|---|---|---|---|---|---|---|---|---|---|
| Vehicle | 100.0% | | 11.0 | | 3.08 ± 0.90 | | 1.67 ± 1.25 | | 98.2% ± 9.3 | |
| ACTH + β-end | 0.0% | <0.0001[2] 0.0040[3] | >20.0[1] | <0.0001[2] 0.0144[3] | 0.00 ± 0.00 | <0.0001[2] 0.0143[3] | 0.00 ± 0.00 | <0.0001[2] 0.0146[3] | 110.5% ± 10.7% | 0.0063[2] 0.0042[3] |
| FTY720 | 41.7% | 0.0004[2] | >20.0[1] | <0.0001[2] | 0.92 ± 1.16 | 0.0003[2] | 0.79 ± 1.01 | 0.0778[2] | 98.3% ± 7.8% | 0.9711[2] |

[1]Median day of onset cannot be calculated if ≤50% of mice developed disease
[2]Compared to vehicle
[3]Compared to FTY720, 3 mg/kg equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

The 8 KB ASCII text file named 1958854-00152_Sequence_Listing-ST25.txt, created Mar. 12, 2020, is incorporated herein by reference.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method of treating an inflammatory, autoimmune, neurologic disease or disorder comprising administering a clinically effective amount of adrenocorticotropic hormone (ACTH) and β-endorphin, to a person in need thereof, wherein the person in need thereof has multiple sclerosis.

2. The method of claim 1, wherein treating comprises resolving an acute exacerbation of the disease.

3. The method of claim 1, wherein treating comprises maintenance therapy, whereby incidences or severity of exacerbations of the disease is reduced.

4. The method of claim 3, wherein the disease is relapsing-remitting multiple sclerosis and the incidence or severity of relapses is reduced.

5. The method of claim 1 comprising administering 40-120 units of ACTH.

6. The method of claim 5, wherein the mass ratio of ACTH:β-endorphin is 2:1.

7. The method of claim 1 comprising administering 0.8-1.2 mg of ACTH.

8. The method of claim 7, wherein the mass ratio of ACTH:β-endorphin is 2:1.

* * * * *